US010875955B2

(12) United States Patent
Kennedy et al.

(10) Patent No.: US 10,875,955 B2
(45) Date of Patent: Dec. 29, 2020

(54) INITIATORS FOR LIVING CARBOCATIONIC POLYMERIZATION

(71) Applicants: Joseph Kennedy, Akron, OH (US);
Turgut Nugay, Istanbul (TR)

(72) Inventors: Joseph Kennedy, Akron, OH (US);
Turgut Nugay, Istanbul (TR)

(73) Assignee: The University of Akron, Ohio, Akron, OH (US)

( * ) Notice: Subject to any disclaimer, the term of this patent is extended or adjusted under 35 U.S.C. 154(b) by 0 days.

(21) Appl. No.: 16/541,502

(22) Filed: Aug. 15, 2019

(65) Prior Publication Data

US 2019/0367664 A1 Dec. 5, 2019

Related U.S. Application Data

(62) Division of application No. 16/069,659, filed as application No. PCT/US2017/014280 on Jan. 20, 2017, now Pat. No. 10,472,457.

(60) Provisional application No. 62/281,243, filed on Jan. 21, 2016, provisional application No. 62/404,418, filed on Oct. 5, 2016.

(51) Int. Cl.

| | | |
|---|---|---|
| *C08F 2/46* | (2006.01) | |
| *C08F 2/50* | (2006.01) | |
| *C08G 61/04* | (2006.01) | |
| *C08G 18/62* | (2006.01) | |
| *C07C 23/18* | (2006.01) | |
| *C07C 13/44* | (2006.01) | |
| *C07C 33/36* | (2006.01) | |
| *C07C 211/27* | (2006.01) | |
| *C07C 35/44* | (2006.01) | |
| *C07C 35/31* | (2006.01) | |
| *C07C 43/188* | (2006.01) | |
| *C07C 35/37* | (2006.01) | |
| *C07C 23/32* | (2006.01) | |
| *C08G 81/02* | (2006.01) | |
| *C08F 2/48* | (2006.01) | |
| *C08F 8/06* | (2006.01) | |
| *C08F 8/30* | (2006.01) | |
| *C08F 210/10* | (2006.01) | |

(52) U.S. Cl.
CPC .......... *C08G 18/6204* (2013.01); *C07C 13/44* (2013.01); *C07C 23/18* (2013.01); *C07C 23/32* (2013.01); *C07C 33/36* (2013.01); *C07C 35/31* (2013.01); *C07C 35/37* (2013.01); *C07C 35/44* (2013.01); *C07C 43/188* (2013.01); *C07C 211/27* (2013.01); *C08G 81/024* (2013.01); *C07C 2602/06* (2017.05); *C07C 2603/08* (2017.05); *C07C 2603/40* (2017.05); *C08F 2/48* (2013.01); *C08F 8/06* (2013.01); *C08F 8/30* (2013.01); *C08F 210/10* (2013.01)

(58) Field of Classification Search
CPC .. C08G 18/6204; C08G 81/024; C08G 1/024; C07C 43/188; C07C 33/36; C07C 13/44; C07C 35/31; C07C 35/37; C07C 23/32; C07C 2602/06; C07C 2603/40; C07C 2603/08; C07C 211/27; C07C 23/18; C07C 35/44; C08F 2/48; C08F 8/30; C08F 210/10; C08F 8/06
USPC ......... 522/140, 139, 136, 135, 134, 1, 71, 6, 522/189, 184; 520/1
See application file for complete search history.

(56) References Cited

U.S. PATENT DOCUMENTS

| | | | |
|---|---|---|---|
| 8,889,926 B2 | 11/2014 | Kennedy et al. | |
| 10,472,457 B2 * | 11/2019 | Kennedy | ............ C08G 18/6204 |
| 2007/0015717 A1 | 1/2007 | Curley, Jr. et al. | |
| 2007/0260019 A1 | 11/2007 | Ohme et al. | |
| 2015/0191566 A1 | 7/2015 | Akron | |
| 2015/0315174 A1 | 11/2015 | Harth et al. | |
| 2016/0002373 A1 | 1/2016 | Kennedy et al. | |
| 2017/0260318 A1 * | 9/2017 | Kennedy | .............. C08G 18/758 |

FOREIGN PATENT DOCUMENTS

WO    WO-2017033158 A1 *  3/2017  ............ F16B 41/005

OTHER PUBLICATIONS

Moorthy et al, Photochemistry of dicarbonyl-substituted benzenes: influence of steric and electronic factors in the cyclization and Diels-Alder trapping reactions of photoenols, ARKIVOC, 2007, viii, 324-340 (Year: 2007).*

Uera, K. et al.; Molecular Orbital Calculation of the Elastic Modulus and the Dielectric Constant for Ultra-Low-k Oraganic Polymers. Japanese Journal of Applied Physics, vol. 43, No. 2, 2004, pp. 504-507; abstract.

PUBCHEM. CID 102112286. Dec. 24, 2015, pp. 1-7 [online], [retrieved on Mar. 7, 2017] https://pubchem.ncbi.nim.nih.gov/compound/102112286#section=Top>; p. 3.

(Continued)

*Primary Examiner* — Jessica Whiteley
(74) *Attorney, Agent, or Firm* — Renner Kenner Greive Bobak Taylor & Weber

(57) ABSTRACT

In various embodiments, the present invention is directed to new low cost initiator compositions for use with the production of well-defined telechelic PIBs (by LC⁺P of isobutylene). In various other embodiments, the present invention is directed to methods for using these novel compositions as initiators for isobutylene (IB) and other cationically polymerizable monomers, such as styrene and its derivatives. In still other embodiments, the present invention is directed to structurally new, allyl (and chlorine) telechelic PIBs formed from these new initiator compositions and their derivatives (in particular, hydroxyl telechelic PIB and amine telechelic PIB). In yet other embodiments, the present invention is directed to structurally new polyurethanes, polyureas, and polyurethane ureas made using telechelic PIBs formed from these new initiator compositions.

14 Claims, 9 Drawing Sheets

(56) References Cited

OTHER PUBLICATIONS

Menta, G., et al.; Recent chemistry of benzocyclobutenes, Tetrahedron vol. 57, No. 4, pp. 625-659, p. 626, col. 1, scheme 4.
Jarugu Narasimha Moorthy; Subhas Samanta; Photochemistry of dicarbonyl-substituted benzenes: influence of steric and electronic factors in the cyclization and Diels-Alder trapping reactions of photoenols; Department of Chemistry, Indian Institute of Technology, Kanpur 208016, India; pp. 324-340.

* cited by examiner

INITIATORS FOR LIVING CARBOCATIONIC POLYMERIZATION

CROSS REFERENCE TO RELATED APPLICATIONS

This application is a divisional application of U.S. patent application Ser. No. 16/069,659, filed Jul. 12, 2018, pending, which is a 371 national phase patent application of International Patent Application No. PCT/US17/14280, filed Jan. 20, 2017, expired, which claims the benefit of U.S. Provisional Patent Application Ser. No. 62/404,418, filed Oct. 5, 2016, and also claims the benefit of U.S. Provisional Patent Application Ser. No. 62/281,243, filed Jan. 21, 2016, all of which are incorporated herein by reference in their entirety.

FIELD OF THE INVENTION

One or more embodiments of the present invention relates to a novel initiator for living carbocationic polymerizations (LC$^+$Ps). In certain embodiments, the present invention relates to novel monofunctional, difunctional and trifunctional LC$^+$P initiators, methods for their synthesis, and polymers made therefrom.

BACKGROUND OF THE INVENTION

Carbocationic polymerizations in general and living carbocationic polymerizations in particular are of great scientific and practical importance for the creation of useful materials. Living carbocationic polymerizations (LC$^+$Ps) proceed in the absence of chain transfer and termination (collectively termed chain breaking) and lead to well-defined designed useful polymers; LC$^+$Ps lead to predetermined degrees of polymerization (molecular weights), narrow molecular weight distributions, desirable end-groups, and sequential (block, graft, etc.) polymers. The mechanism of LC$^+$Ps is well known in the art. (See, *Designed Polymers by Carbocationic Macromolecular Engineering*, by J. P. Kennedy and B. Ivan, Hanser pub, 1992, the disclosure of which is incorporated herein by reference in its entirety). The chemistry of initiation of cationic polymerizations is discussed in detail in *Carbocationic Polymerization*, by J. P. Kennedy and E Marechal, Wiley, 1982, pp. 81-116, and specifically that of LC$^+$P, pp 9-31, the disclosure of which is incorporated herein by reference in its entirety.

The initiator that is used world-wide for the production of well-defined telechelic FIBS (by LC$^+$P of isobutylene) by academic and industrial investigators, is 5-tert-butyl-1,3-bis (1-chloro-1-methylethyl)benzene (abbreviated herein as HDCCl, for hindered dicumyl chloride):

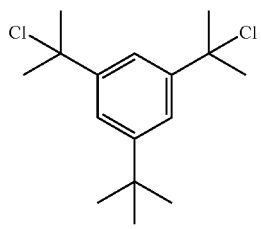

5-tert-butyl-1,3-bis(1-chloro-1-methylethyl)benzene (HDCCl) (I)

Other initiators commonly used for the synthesis of well-defined telechelic PIBs (by LC$^+$P of isobutylene) include those described in U.S. Pat. No. 5,733,998 to Kennedy et al. and U.S. Pat. No. 8,889,926 to Kennedy et al., the disclosure of which are incorporated herein by reference in their entirety.

The synthesis of HDCCl occurs in several steps and requires the use of an expensive starting material and costly reagents. (See, Wang, B., Mishra, M. K., Kennedy J. P., *Polymer Bulletin*, 17, 205 (1987), the disclosure of which is incorporated herein by reference in its entirety.) HDCCl in conjunction with Friedel-Crafts acid co-initiators, e.g., TiCl$_4$, instantaneously initiates bi-directional LC$^+$P of isobutylene. The bulky tert butyl group in HDCCl is necessary as it prevents unacceptable intramolecular aromatic alkylation by the tert cation that arises by the first incorporated isobutylene molecule; in other words, in the absence of the tertbutyl group in HDCCl unacceptable facile zero order intramolecular aromatic alkylation by the first aliphatic tert cation would occur leading to an indanyl ring plus a proton as shown in Scheme 1 below.

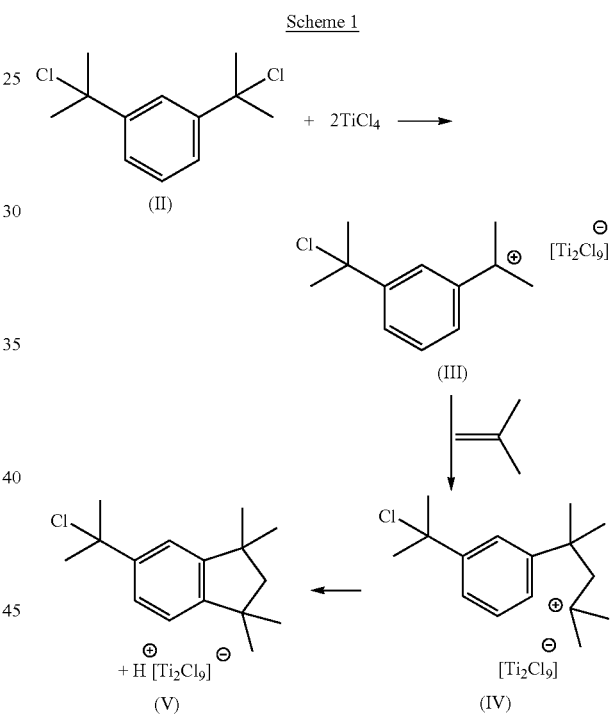

If such intramolecular aromatic alkylation occurs, which is in fact a chain transfer reaction, LC$^+$P cannot take place because the expelled proton (see last formula in the above equation) would initiate polymerization and would lead to polymers with useless "sterile" H-head group.

Accordingly, what is needed in the art is a low cost LC$^+$P initiator that in conjunction with a Friedel-Crafts acid co-initiators, such as TiCl$_4$, initiates LC$^+$P of isobutylene.

SUMMARY OF THE INVENTION

In various embodiments, the present invention is directed to new low cost initiator compositions for use with the production of well-defined telechelic PIBs (by LC$^+$P of isobutylene). In various other embodiments, the present invention is directed to methods for using these novel compositions as initiators for isobutylene (IB) and other cationically polymerizable monomers, such as styrene and its derivatives. In still other embodiments, the present invention is directed to structurally new, allyl (and chlorine) telechelic PIBs formed from these new initiator compositions and their derivatives (in particular, hydroxyl telechelic PIB (HO-PIB-OH) for the production of new polyurethanes and amine telechelic PIB (H₂N-PIB-NH₂) for the production of polyrueas). In yet other embodiments, the present invention is directed to structurally new polyurethanes, polyureas, and polyurethane ureas made using telechelic PIBs formed from these new initiator compositions.

In a first aspect, the present invention is directed to an initiator molecule defined by one of the following formulas:

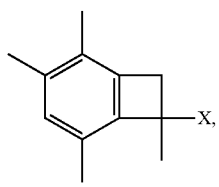
(VI)

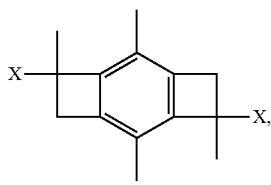
(VII)

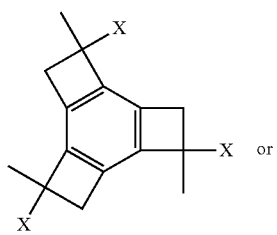
(VIII) or

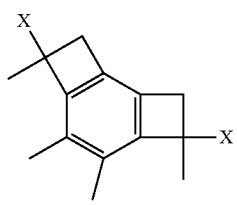
(IX)

where each x is Cl, OH, or OCH₃. In one or more of these embodiments, the initiator molecule is a monofunctional, bifunctional or trifunctional initiator.

In one or more embodiments, the initiator molecule of the present invention includes any one or more of the above referenced embodiments of the first aspect of the present invention wherein the initiator molecule is a monofunctional initiator having the formula:

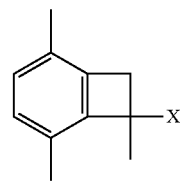
(VI)

wherein x is Cl, OH, or OCH₃.

In one or more embodiments, the initiator molecule of the present invention includes any one or more of the above referenced embodiments of the first aspect of the present invention wherein the initiator molecule is a bifunctional initiator having the formula:

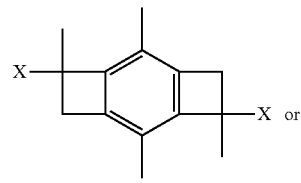
(VII)

or

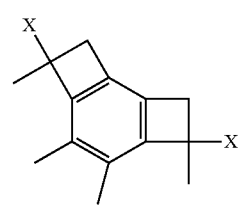
(IX)

wherein x is Cl, OH, or OCH₃.

In one or more embodiments, the initiator molecule of the present invention includes any one or more of the above referenced embodiments of the first aspect of the present invention wherein the initiator molecule is a trifunctional initiator having the formula:

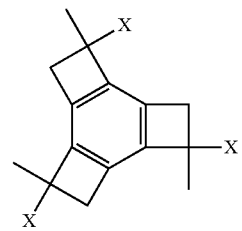
(VIII)

wherein x is Cl, OH, or OCH₃.

In one or more embodiments, the initiator molecule of the present invention includes any one or more of the above referenced embodiments of the first aspect of the present invention wherein the initiator molecule is defined by the chemical formula 2,4,7,9-tetramethyl-tricyclo[6.2.0.0³,⁶]deca-1(8),2,6-triene-4,9-diol or 4,9-dichloro-2,4,7,9-tetramethyl-tricyclo[6.2.0.0³,⁶]deca-1(8),2,6-triene.

In a second aspect, the present invention is directed to a telechelic polyisobutylene composition comprising one, two, or three polyisobutylene chains extending from the residue of an initiator as molecule as claimed in claim 1. In some of these embodiments, each of the one, two, or three polyisobutylene chains further comprises a terminal functional group. In one or more of these embodiments, the terminal functional groups are selected from the group consisting of allyl groups, hydroxyl groups, primary or tertiary alcohols, halides, amine groups, azide groups, thiol groups, furanyl groups, alkynyl groups, cyano groups, and combinations thereof.

In a third aspect, the present invention is directed to an allyl-telechelic polyisobutylene composition comprising a residue of the initiator of claim 1. In one or more of these embodiments, the allyl-telechelic polyisobutylene composition comprises one, two or three allyl-telechelic polyisobutylene chains extending from the initiator residue. In one or more of these embodiments the allyl-telechelic polyisobutylene composition has the formula:

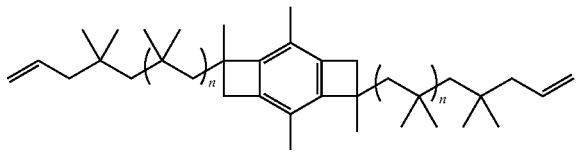

(X)

wherein each individual n is an integer from 2 to about 5,000.

In a fourth aspect, the present invention is directed to a primary alcohol terminated polyisobutylene comprising a residue of the novel initiator described above. In some of these embodiments, the primary alcohol terminated polyisobutylene comprising one, two or three primary alcohol terminated polyisobutylene chains extending from the initiator residue. In one or more embodiment, the primary alcohol terminated polyisobutylene has the formula:

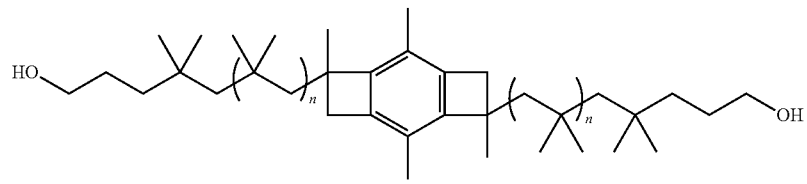

(XI)

wherein each individually n is an integer from 2 to 5,000.

In a fifth aspect, the present invention is directed to an amine terminated polyisobutylene comprising a residue of the novel initiator described above. In some of these embodiments, the amine terminated polyisobutylene has the formula:

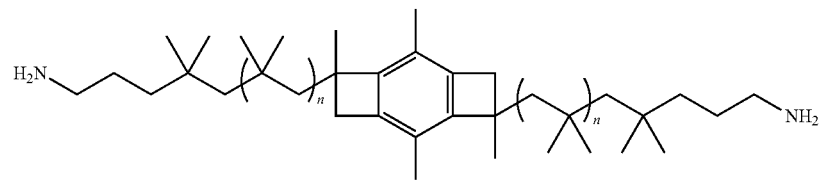

(XII)

wherein each individual n is an integer from 2 to 5,000.

In a sixth aspect, the present invention is directed to a polyisobutylene-based polyurethane and/or polyurea comprising a residue of the initiator described above. In some of these embodiments, the polyisobutylene-based polyurethane and/or polyurea has the formula:

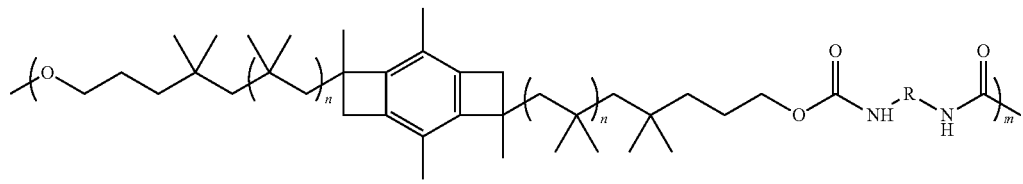

(XIII)

where each n is an integer from 2 to 5,000, m is an integer from 2 to 1,000,000, and R is a residue of toluene diisocyanate or 4, 4'-diphenylmethane diisocyanate having the formula:

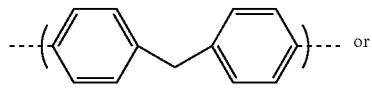   or

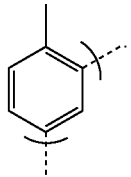

(XIV)

(XV)

In some other of these embodiments, the polyisobutylene-based polyurethane and/or polyurea has the formula:

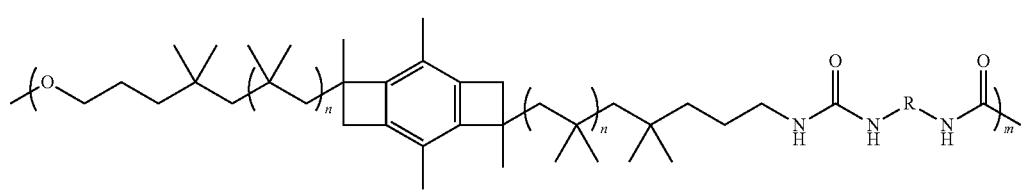

(XVI)

where each n is an integer from 2 to 5,000, m is an integer from 2 to 1,000,000, and R is a residue of toluene diisocyanate or 4, 4'-diphenylmethane diisocyanate having the formula:

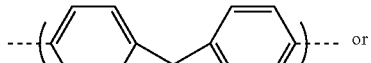   or

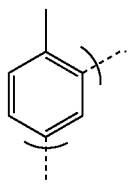

(XIV)

(XV)

In a seventh aspect, the present invention is directed to a polyisobutylene-based polyurethane comprising the reaction product of a diisocyanate and a primary alcohol terminated polyisobutylene comprising a residue of the novel initiator described above. In some of these embodiments, the primary alcohol terminated polyisobutylene further comprises one, two or three primary alcohol terminated polyisobutylene chains extending from the initiator residue. In one or more of these embodiments, the primary alcohol terminated polyisobutylene has the formula:

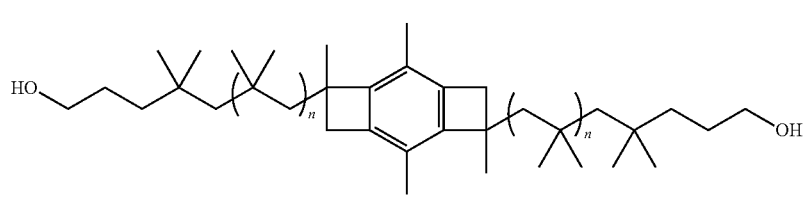

(XI)

wherein each individual n is an integer from 2 to 5,000.

In an eighth aspect, the present invention is directed to a polyisobutylene-based polyurea comprising the reaction product of a diisocyanate and an amine terminated polyisobutylene comprising a residue of the initiator of claim 1. In some of these embodiments, the amine terminated polyisobutylene has the formula:

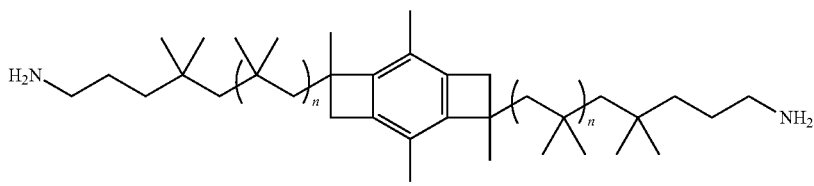

(XII)

wherein each individual n is an integer from 2 to 5,000.

In a ninth aspect, the present invention is directed to a method form making the novel initiator molecule described above comprising: dissolving 1,2,4,5-tetramethyl benzene or 1,2,3,5-tetramethyl benzene in a suitable solvent; combining an acetyl halide, aluminum chloride, and a dry solvent in a suitable container and heating it to reflux for from about 6 to about 12 hours; adding the 1,2,4,5-tetramethyl benzene or 1,2,3,5-tetramethyl benzene to the acetyl halide solution and stirring at reflux for an additional 10 to 14 hours; separating the resulting polymer containing solution into organic and aqueous phases, washing the resulting organic phase with aqueous sodium carbonate, removing the solvent, and drying the resulting product to produce the corresponding diethanone; dissolving the corresponding diethanone in a suitable solvent and irradiating it with ultraviolet light to form the corresponding bis-benzocyclobutenol initiator molecule. In some of these embodiments, the method further comprises the step of hydrochlorinating the bis-benzocyclobutenol initiator molecule to form the corresponding dichloro initiator molecule.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1:
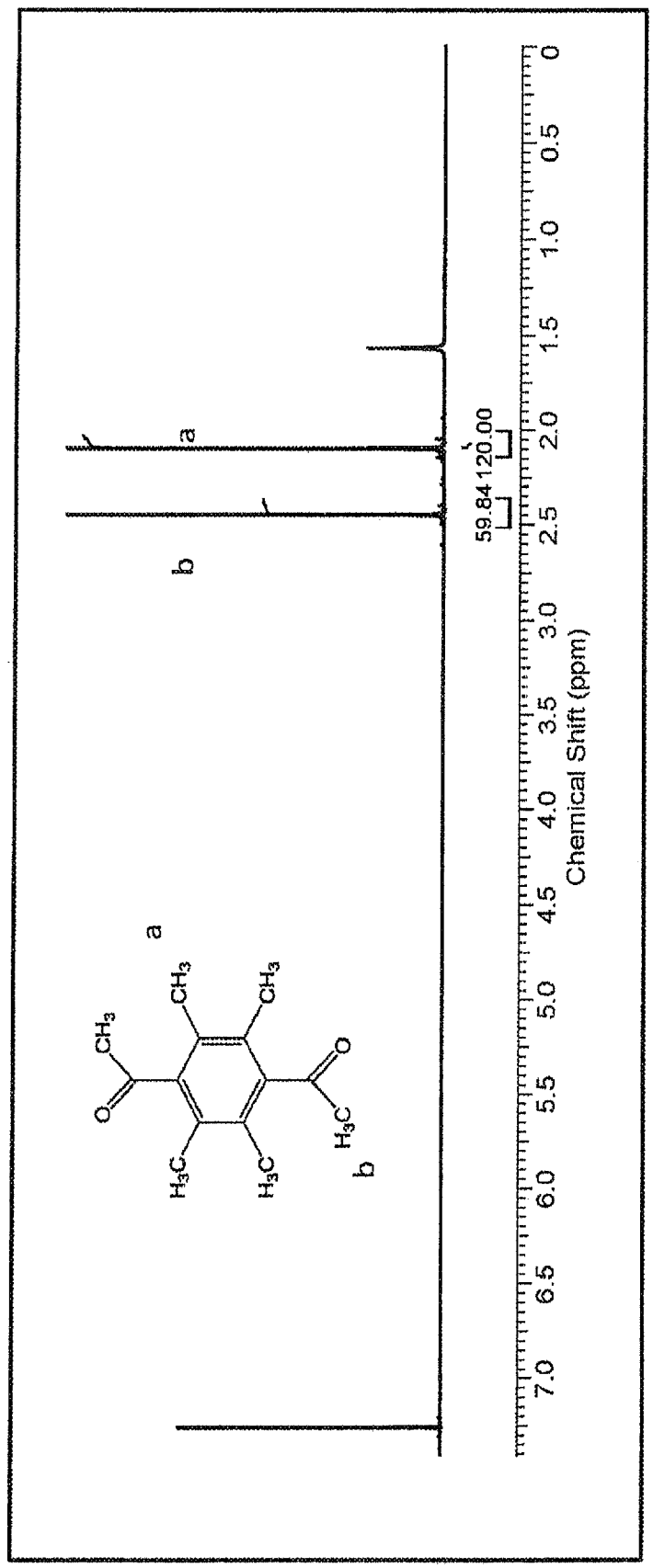
FIG. 1 is an $H^1$NMR spectrum of 1,1'-(2,3,5,6-tetramethyl-1,4-phenylene)diethanone (diacetyl durene, DAD).

In various embodiments, the present invention is directed to new low cost initiator compositions for use with the production of well-defined telechelic PIBs (by LC$^+$P of isobutylene). In various other embodiments, the present invention is directed to methods for using these novel compositions as initiators for isobutylene (IB) and other cationically polymerizable monomers, such as styrene and its derivatives. In still other embodiments, the present invention is directed to structurally new, allyl (and chlorine) telechelic PIBs formed from these new initiator compositions and their derivatives (in particular HO-PIB-OH for the production of new polyurethanes). In yet other embodiments, the present invention is directed to structurally new polyurethanes and polyureas made using telechelic PIBs formed from these new initiator compositions.

In one or more embodiments, the present invention relates to novel low cost LC$^+$P initiator molecules having a central benzene ring surrounded by from 1 to 3 short bridges of tricyclo compounds (cyclo groups) each having at least one functional group that, in the presence of a Friedel-Crafts acid co-initiator, produce well-defined one, two, or three arm telechelic polymers. The following structures are representative of these novel low cost LC$^+$P initiator molecules:

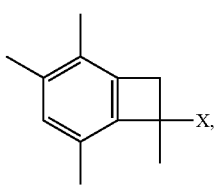

(VI)

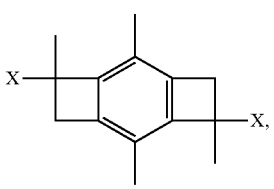

(VII)

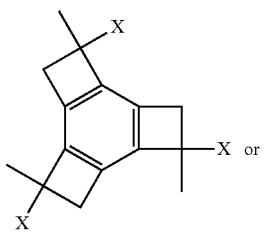

(VIII)

(IX)

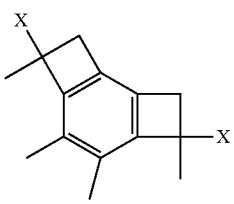

where each x is Cl, OH, or OCH$_3$.

In some embodiments, the present invention relates to two novel low cost LC$^+$P initiator molecules, namely, 2,4,7,9-tetramethyl-tricyclo[6.2.0.0$^{3,6}$]deca-1(8),2,6-triene-4,9-diol (abbreviated herein as bBCB-ol, for bis-benzocyclobutenol), and 4,9-dichloro-2,4,7,9-tetramethyl-tricyclo[6.2.0.0$^{3,6}$]deca-1(8),2,6-triene (abbreviated herein as bBdClCB, for bis-benzo-dichloro-cyclobutenol), that initiate bidirectional LC$^+$P in the presence of Friedel-Crafts acid co-initiators and produce well-defined two arm telechelic polymers. It should be appreciated that the two —CH$_3$ groups on the phenyl ring in these and similar embodiments prevent intramolecular aromatic alkylation and enable LC$^+$P to proceed.

In some other embodiments, the present invention is directed to the corresponding alcohol (i.e., the methoxy derivative—X═O) of molecules (VI), (VII), or (VIII), having the following structures:

(XVII)

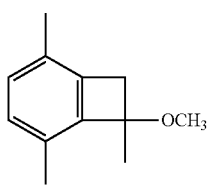

(XVIII)

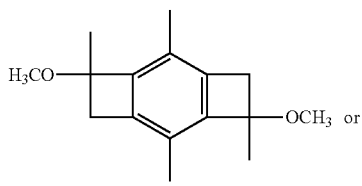

(XIX)

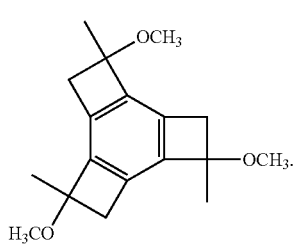

In still other embodiments, the present invention is directed to the corresponding alcohol (i.e., the hydroxyl derivative—X═OH) of molecules (VI), (VII), or (VIII), having the following structures:

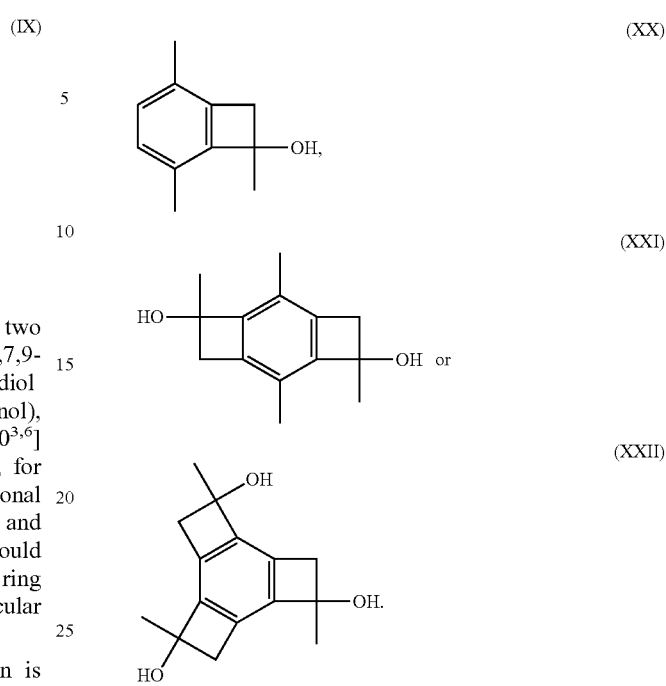

In still other embodiments, novel low cost LC$^+$P initiator molecules according to the present invention may be formed from 1,2,3,5-tetramethyl benzene rather than 1,2,4,5-tetramethylbenzene (durene). In one or more of these embodiments, low cost initiator compositions of the present invention may include, without limitation, initiator molecules made from 1,2,3,5-tetramethyl benzene or having similar structures. In one or more embodiments, the novel low cost LC$^+$P initiator molecules according to the present invention may be formed from 1,2,3,5-tetramethyl benzene and have one of the following structures:

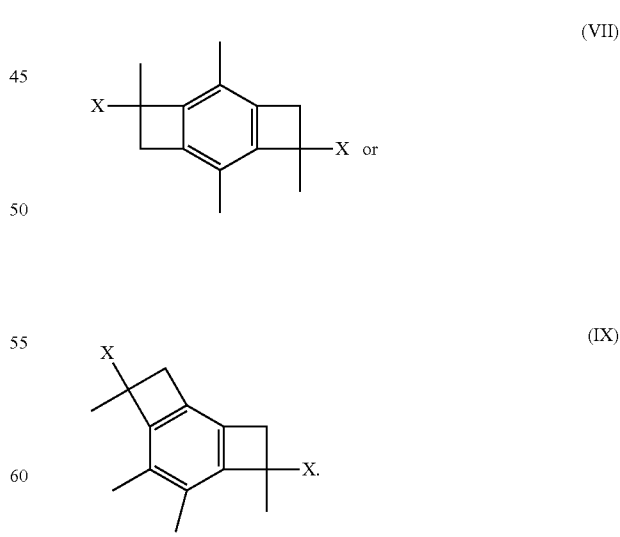

wherein x is Cl, OH, or OCH$_3$.

In various embodiments, the novel low cost LC$^+$P initiator molecules of the present invention may have the formula:

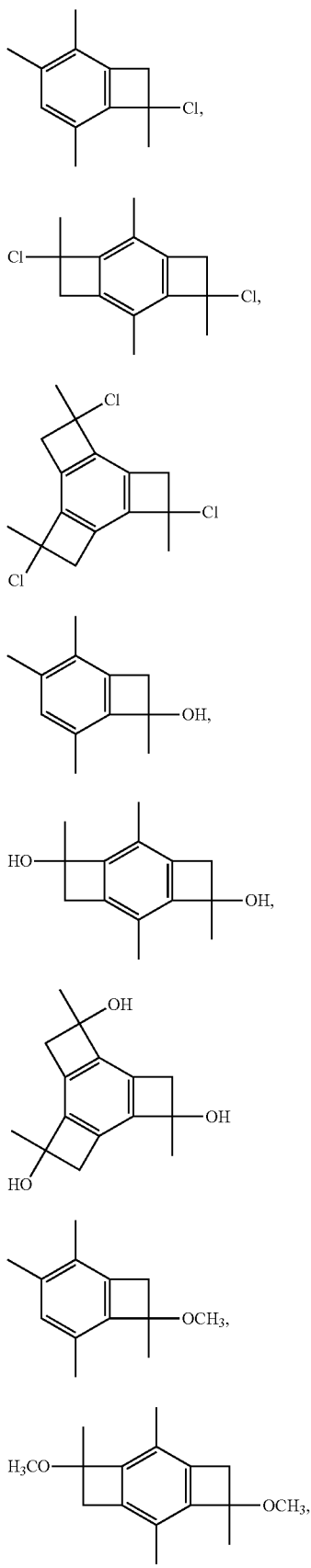

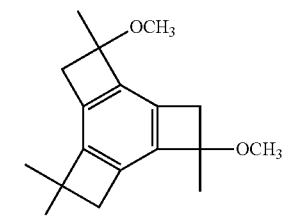

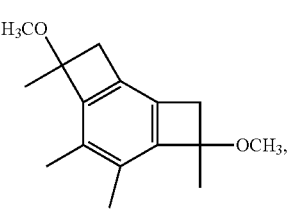

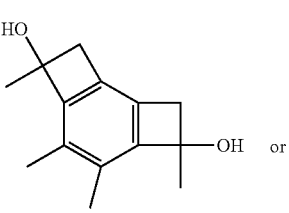

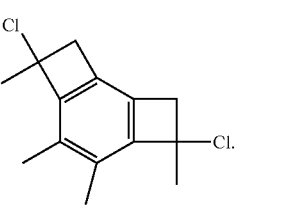

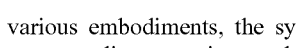

In various embodiments, the synthesis of bi-functional initiators according to various embodiments of the present invention starts with low cost and readily commercially available reactants, namely 1,2,4,5-tetramethylbenzene (durene) or 1,2,3,5-tetramethyl benzene, rather than the much more expensive starting material used for the synthesis of HDCCl, such as 5-tert-butylisophthalic acid (5-tert-butyl-1,3-benzene-dicarboxylicacid) and does not require the use of "costly reagents," such as methymagnesium bromide and HCl gas. 1,2,4,5-tetramethylbenzene (durene) and 1,2,3,5-tetramethyl benzene are commercially available from numerous sources including Sigma-Aldrich (St. Louis Mo.), AKos Consulting & Solutions GmbH (Germany), and Tokyo Chemical Industry Co., Ltd. (TCI) (Japan). Further this process is much simpler (i.e. it requires less steps) and consequently it is less costly than that of HDCCl.

As used herein, the term "bifunctional initiator(s)" or "bifunctional initiator molecule" or "bifunctional molecule" are used interchangeably to refer to an initiator molecule that initiates bidirectional LC$^+$P in the presence of Friedel-Crafts acid co-initiators to produce well-defined two arm telechelic polymers. Likewise, as used herein the terms "monofunctional initiator(s)" or "monofunctional initiator molecule" or "monofunctional molecule" are used interchangeably to refer to an initiator molecule that initiates monodirectional LC$^+$P in the presence of Friedel-Crafts acid co-initiators to produce well-defined single arm telechelic polymers. Similarly, as used herein the terms "trifunctional initiator(s)" or "trifunctional initiator molecule" or "trifunctional molecule" are used interchangeably to refer to an initiator molecule that initiates tridirectional LC+P in the presence of Friedel-Crafts acid co-initiators to produce well-defined three arm telechelic polymers.

Scheme 2 below outlines the syntheses of bBCB-ol and its conversion to bBdClCB and is generally representative of the process:

Scheme 2

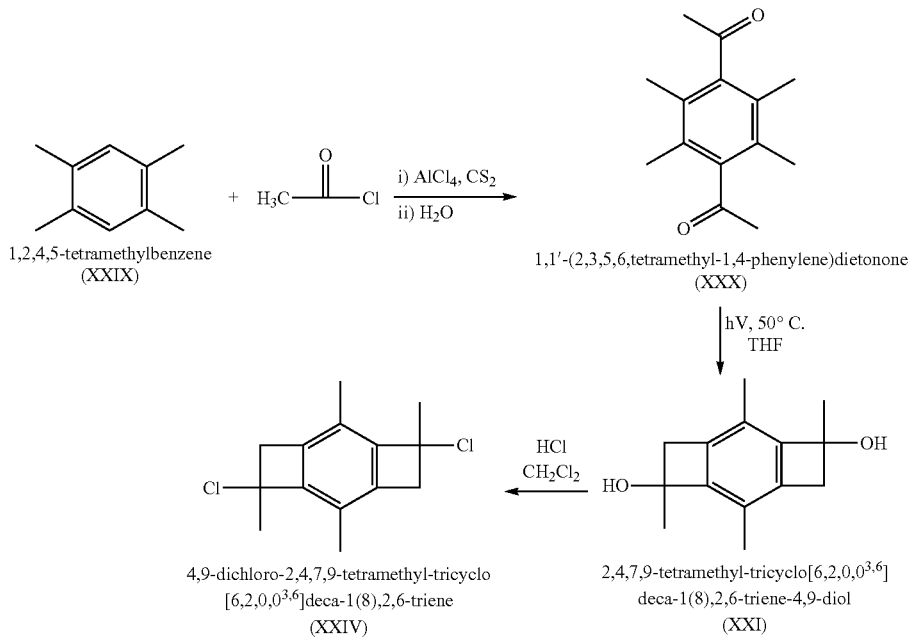

1,2,4,5-tetramethylbenzene
(XXIX)

1,1'-(2,3,5,6,tetramethyl-1,4-phenylene)dietonone
(XXX)

2,4,7,9-tetramethyl-tricyclo[6,2,0,0$^{3,6}$]deca-1(8),2,6-triene-4,9-diol
(XXI)

4,9-dichloro-2,4,7,9-tetramethyl-tricyclo[6,2,0,0$^{3,6}$]deca-1(8),2,6-triene
(XXIV)

In Scheme 2, above, the starting material is durene (XXIX), but the invention is not so limited and suitable starting materials may also include, without limitation, 1,2,4,5-tetramethyl benzene and 1,2,3,5-tetramethyl benzene. The first step involves the Friedel-Crafts diacylation of the starting material with an acetyl halide, such as acetyl chloride (AcCl), acetyl bromide, or acetic anhydride in the presence of aluminum chloride (AlCl$_3$) or a similar Lewis acid, such as FeCl$_3$ or AlBr$_3$, in a suitable solvent such as CS$_2$, dichloromethane, chloroform, chlorobenzene, or nitromathane. (See, e.g., Pinkus A. G., Kalyanam N., *Organic Preparations and Procedures Int*, 10 (6), 255, 1978 and Andreou A. D., Bulbulian R. V., Gore P. H., Tetrahedron, 36, 2101, 1980 the disclosures of which is incorporated herein by reference in its entirety) and (ii) separating the resulting polymer containing solution into organic and aqueous phases, washing the resulting organic phase with aqueous sodium carbonate (see, Scheme 2) and water, removing the solvent and drying the resulting product to produce the corresponding diethanone, 1,1'-(2,3,5,6-tetramethyl-1,4phenylene) diethanone (diacetyl durene, (DAD)) (molecule (XXX) in Scheme 2).

In one or more embodiments, the ratio of AlCl$_3$/AcCl/ starting material (durene) was in the range of 6-7:3-5:1.

In one or more embodiments, the AcCl, AlCl$_3$, and dry CS$_2$ were placed (in this sequence and under a nitrogen atmosphere) in a vessel equipped with a condenser, mechanical stirrer, and three-way valve, heated to reflux and stirred for from about 6 to about 12 hours before the starting material (dissolved in CS$_2$) was added and stirring continued at reflux for an additional 10 to 14 hours (overnight). In some embodiments, the AcCl, AlCl$_3$, and dry CS$_2$ were heated to reflux and stirred for from about 6 to about 10 hours, in other embodiments, from about 7 to about 10 hours and in other embodiments, from about 8 to about 9 hours before the starting material (dissolved in CS$_2$) was added. In some embodiments, the AcCl, AlCl$_3$, dry CS$_2$ and starting material were stirred at reflux for from about 2 to about 5 hours, in other embodiments, 4 to about 6 hours, in other embodiments, 5 to about 7 hours, in other embodiments, 6 to about 8 hours, in other embodiments, 9 to about 11 hours, in other embodiments, 10 to about 12 hours, in other embodiments, 10 to about 12 hours, in other embodiments, from about 12 to about 14 hours and in other embodiments, from about 11 to about 13 hours after the starting material (dissolved in CS$_2$) was added.

In one or more of these embodiments, the diacetyl durene (XII) containing solution is then separated into organic and aqueous phases by pouring the diacetyl durene solution onto crushed ice, acidifying it with concentrated aqueous hydrochloric acid, and then adding methylene chloride.

In one or more of these embodiments, after being washed in a aq. sodium carbonate (see, Scheme 2), the polymer containing organic phase is then dried over anhydrous sodium sulfate for from about 1.5 to about 4 hours, in other embodiments, from about 2 to about 4 hours, and in other embodiments, from about 2 to about 3 hours. In one or more of these embodiments, the solvent may be removed by rotary evaporation and the white solid was recrystallized from solvent, such as, diethyl ether or, in other embodiments, benzene (See, Example 1, below). The choice of recrystallization solvent will depend upon the particular product being produced and one of ordinary skill in the art will be able to select a suitable recrystallization solvent without undue experimentation.

In a second step, the corresponding diethanone molecule (diacetyl durene, (DAD), molecule (XXX) in Scheme 2) is dissolved in a suitable solvent, such as benzene or tetrahydrofuran (THF) and irradiated with ultraviolet light for a period of from about 48 hours to about 96 hours at a temperature of from about 40° C. to about 60° C. to form the corresponding bis-benzocyclobutenol. In the embodiment of Scheme 2, the bis-benzocyclobutenol is 2,4,7,9-tetramethyl-tricyclo[6.2.0.0$^{3,6}$]deca-1(8),2,6-triene-4,9-diol (bBCB-ol) (molecule (XXI) in Scheme 2).

In some of these embodiments, diethanone molecule (XXX) may be irradiated with ultraviolet light having a wavelength of from about 290 nm to about 340 nm for a period of from about 55 hours to about 96 hours. In some embodiments, the diethanone molecule (XXX) may be irradiated with ultraviolet light having a wavelength of from about 290 nm to about 330 nm, in other embodiments, from about 290 nm to about 320 nm, in other embodiments, from about 290 nm to about 310 nm, in other embodiments, from about 295 nm to about 330 nm, in other embodiments, from about 295 nm to about 315 nm, and in other embodiments, from about 295 nm to about 315 nm. In some embodiments, the diethanone molecule (XXX) may be irradiated with ultraviolet light having a wavelength of about 300 nm.

In some embodiments, the diethanone molecule (XXX) may be irradiated with ultraviolet light from about 65 hours to about 96, in other embodiments, from about 75 hours to about 96, in other embodiments, from about 48 hours to about 85, and in other embodiments, from about 48 hours to about 75. In some of these embodiments, corresponding diethanone (XXX) may be irradiated with ultraviolet light for at a temperature of from about 45° C. to about 60° C., in other embodiments, from about 50° C. to about 60° C., in other embodiments, from about 55° C. to about 60° C., in other embodiments, from about 40° C. to about 55° C., in other embodiments, from about 40° C. to about 50° C., in other embodiments, from about 40° C. to about 60° C., and in other embodiments, from about 45° C. to about 55° C. In some of these embodiments, the diethanone (XXX) is irradiated with ultraviolet light for a period of about 72 hours at a temperature of about 50° C.

Figure 2:
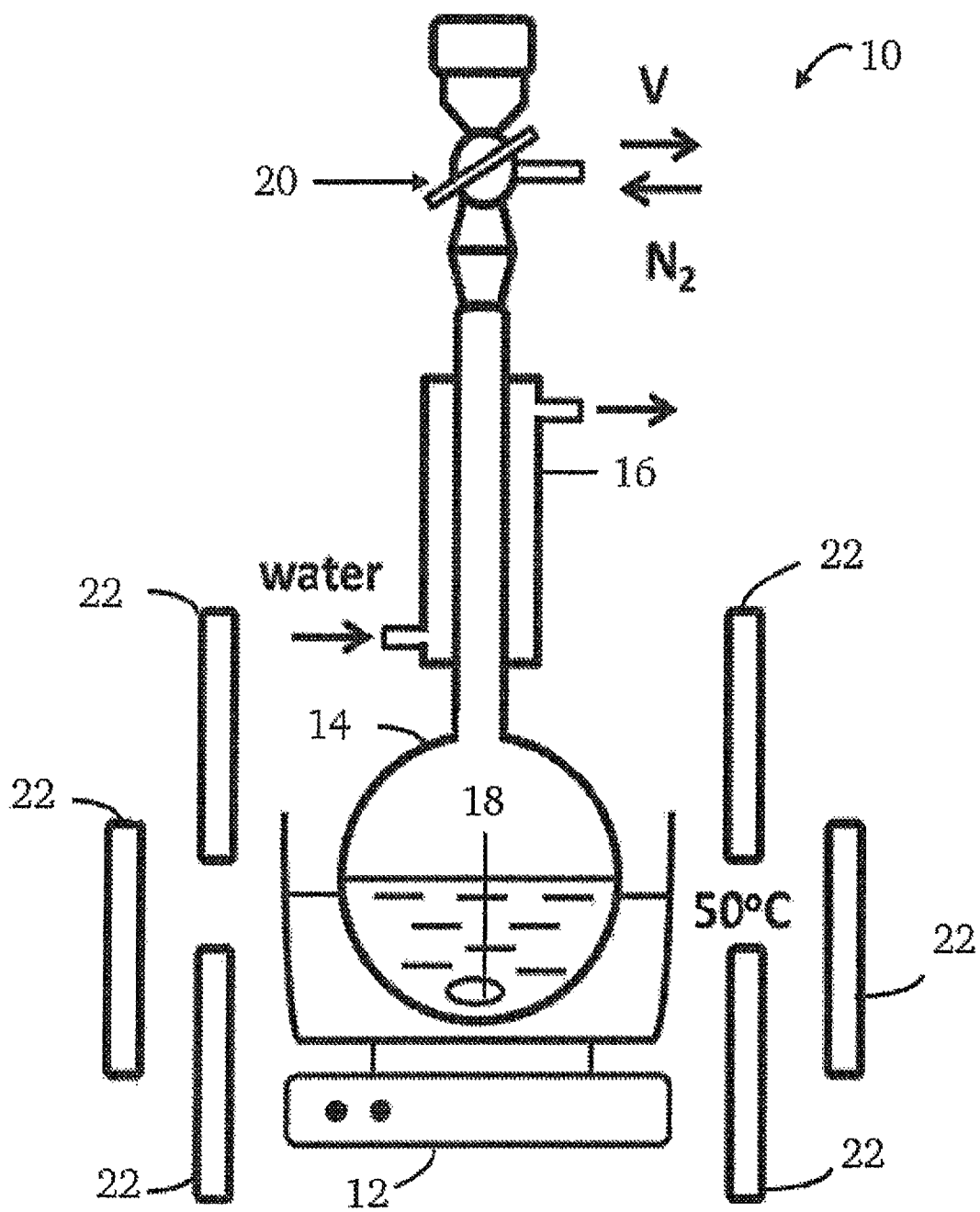
FIG. 2 is a schematic diagram of a photolysis apparatus for the synthesis of 2,4,7,9-tetramethyl-tricyclo[6.2.0.0$^{3,6}$] deca-1(8),2,6-triene-4,9-diol (bBCB-ol).

In one or more embodiments, this step may be carried out using the photolysis apparatus 10 shown in FIG. 2. As can be seen, photolysis apparatus 10 shown in FIG. 2 comprises a heating element 12, round bottom flask 14, reflux condenser 16, a magnetic stirring bar 18, 2 way valve 20, and a plurality of UV lamps 22. In the embodiment shown in FIG. 2, the plurality of UV lamps 22 comprises six 9 watt, 300 nm broad band UV lamps.

In some embodiments, the bis-benzocyclobutenol (see, e.g., molecule (XXI) in Scheme 2) may be hydrochlorinated to form the corresponding dichloro compound (see, e.g., molecule (XXIV) in Scheme 2). In the embodiment of Scheme 2, the corresponding bis-benzo-dichloro-cyclobutenol is 4,9-dichloro-2,4,7,9-tetramethyl-tricyclo[6.2.0.0$^{36}$] deca-1(8),2,6-triene (XXIV) (bBdClCB). (See, Example 2, below). However, other suitable methods known in the art for replacing the OH group with a halogen may also be used in some embodiments.

Figure 4:
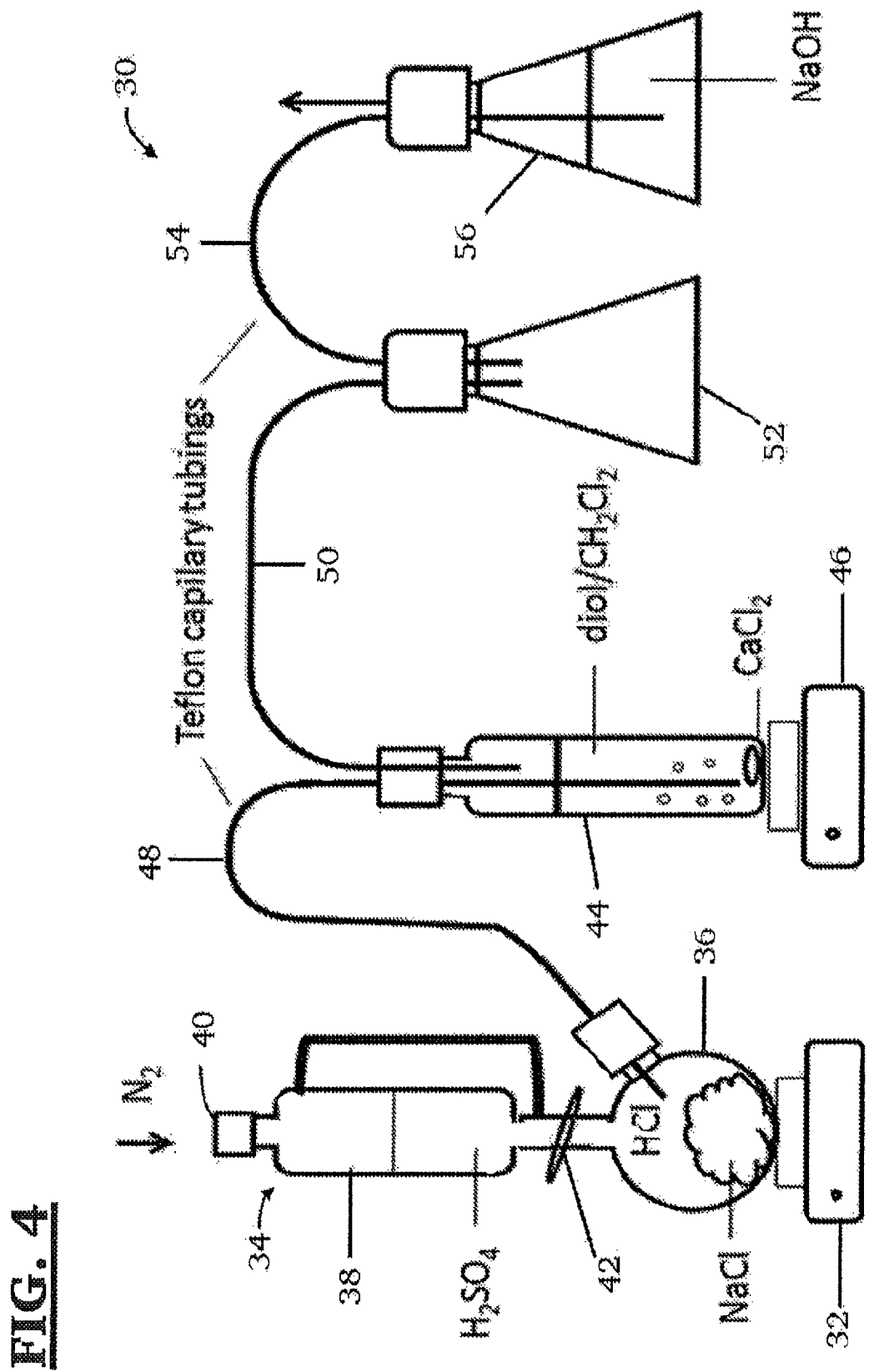
FIG. 4 is a schematic diagram of a chlorination apparatus for use in chlorinating bBCB-ol to form 4,9-dichloro-2,4,7,9-tetramethyl-tricyclo[6.2.0.0$^{3,6}$]deca-1(8),2,6-triene (bBd-ClCB).

In some of these embodiments, the bis-benzocyclobutenol (see, molecule (XXI) in Scheme 2) may be hydrochlorinated using the chlorination apparatus 30 shown in FIG. 4. As can be seen, the hydrochlorination apparatus 30 of FIG. 4 comprises a first heating element 32, in thermal contact with a first reaction vessel 34 having a lower portion 36 containing NaCl, an upper portion 38 containing H$_2$SO$_4$ and including gas inlet valve 40 through which a dry gas, such as nitrogen gas, enters the system, and a valve 42 separating the upper portion 38 and lower portion 36. Valve 42 may be opened to allow the H$_2$SO$_4$ to flow dropwise into the lower portion 36 and onto the NaCl, where it reacts with the NaCl to produce HCl gas. In some of these embodiments, the bis-benzocyclobutenol (see, e.g., molecule (XXI) in Scheme 2) is dissolved in a suitable solvent such as dichloromethane (CH$_2$Cl$_2$) and placed in a second reaction vessel 44 containing CaCl$_2$. Second reaction vessel 44 is in thermal contact with a second heating element 46. A first Teflon capillary tube 48 runs from the lower portion 36 of the first reaction vessel 34 and into second reaction vessel 44. In these embodiments, the HCl gas generated in the reaction vessel 34 is allowed to flow through the first Teflon™ capillary tube 48 into the second reaction vessel 44 and bubble through its contents. The HCl gas then flows out of the second reaction vessel 44 through a second Teflon™ capillary tube 50 into a first flask 52 and then through a third Teflon capillary tube 54 into a second flask 56 containing aqueous NaOH, where it is neutralized.

In one or more of these embodiments, the gaseous HCl is bubbled into the bis-benzocyclobutenol solution in the presence of CaCl$_2$ for from about 4 hours to about 8 hours at a temperature of from about −10° C. to about 10° C. under continuous nitrogen flush. In some embodiments, the gaseous HCl is bubbled into the bis-benzocyclobutenol solution in the presence of CaCl$_2$ from about 4 hours to about 7 hours, in other embodiments, from about 4 hours to about 6 hours, and in other embodiments, from about 6 hours to about 8 hours under continuous nitrogen flush. In some of these embodiments, the gaseous HCl is bubbled into the bis-benzocyclobutenol solution at a temperature of from about −10° C. to about 10° C., in other embodiments, from about −7° C. to about 7° C., and in other embodiments, from about −3° C. to about 3° C. In some of these embodiments, the gaseous HCl was bubbled into the bis-benzocyclobutenol solution in the presence of CaCl$_2$ for six hours at 0° C. under continuous nitrogen flush. In these embodiments, the CaCl$_2$ is removed by filtration and the corresponding dichloro compound (see, e.g., molecule (XXIV) in Scheme 2) is then extracted, dried, and purified according to established methods. (See, Example 3, below).

It is believed that this same strategy can also be used to prepare mono- and tri-functional initiators As used herein, the term "monofunctional initiator(s)" or "monofunctional initiator molecule" or "monofunctional molecule" are used interchangeably to refers to an initiator molecule that instantaneously initiates monodirectional LC$^+$P in the presence of Friedel-Crafts acid co-initiators to produce well-defined single arm telechelic polymers. Likewise, as used herein, the term "trifunctional initiator(s)" or "trifunctional initiator molecule" or "trifunctional molecule" are used interchangeably to refers to an initiator molecule that instantaneously initiates tridirectional LC$^+$P in the presence of Friedel-Crafts acid co-initiators to produce well-defined single arm telechelic polymers.

Suitable starting materials for production of monofunctional initiators using the strategy described above include, without limitation, mono-acetylated durene. Similarly, and as shown in Scheme 3 below, suitable starting materials for production of new trifunctional initiators (for preparation of tri-arm star polymers) using the strategy described above include, without limitation, triacetylated 1,3,5-trimethylbenzene (mesitylene).

Scheme 3

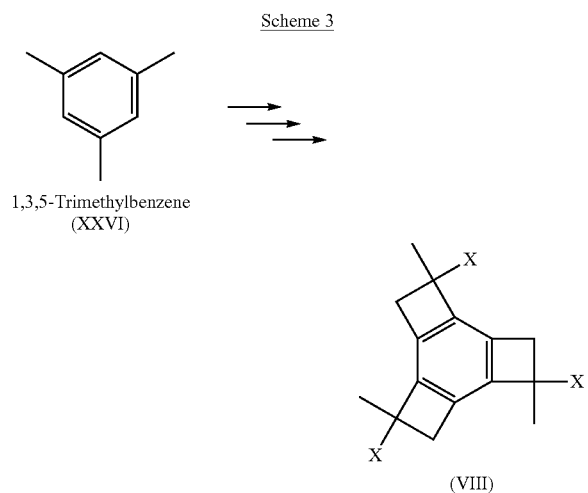

1,3,5-Trimethylbenzene
(XXVI)

(VIII)

where each x is Cl, OH, or OCH$_3$.

As set forth above, it is believed that the low cost novel initiators of the present invention can be used in place of prior art LC$^+$P initiators to make a wide variety of polymers. It should also be appreciated that because these novel initiators, in conjunction with Friedel-Crafts acids, are sources of highly reactive tert carbocations (see Scheme 4, below) they will initiate the polymerization of any cationic monomer known to the art including but not limited to, isobutylene styrenes, butadiene, isoprene, cyclopentadiene, pinenes, and vinylether. (See J. P. Kennedy, Cationic Polymerization of Olefins: A Critical Inventory, Wiley/Interscience pub. 1975, the disclosure of which is incorporated herein by reference in its entirety.) It is believed that the low cost novel initiators of the present invention can be substituted 1 for 1 with the initiators currently in use (including, but not limited to those initiators described in U.S. Pat. Nos. 5,733,998 and 8,889,926, the disclosure of which are incorporated herein by reference in their entirety) for any LC$^+$P reaction producing one, two, or three arm polymers. Furthermore, as these novel initiators become incorporated into the polymers they produce, it is believed that the structures they produce are also novel.

Importantly, in a variety of embodiments, the initiator molecules of the present invention may be used to form functionalized telechelic polyisobutylene compositions comprising one, two, or three polyisobutylene chains extending from the residue of the initiator molecule, each chain having a terminal functional group. A wide variety of terminal functional groups may be added to these telechelic polyisobutylene compositions using conventional techniques. Suitable terminal functional groups may include, without limitation, allyl groups, hydroxyl groups, primary alcohols, halides, amine groups, azide group, thiol group, furanyl group, alkynyl group, cyano group, or a combination thereof.

The low cost bifunctional initiators of the present invention are particularly useful as a substitute for 5-tert-butyl-1,3-bis(1-chloro-1-methylethyl)benzene (HDCCl) (molecule (I)) in the formation of bidirectional telechelic PIB polymers and their derivative polyurethanes and polyureas. In a variety of embodiments, the present invention also includes allyl di-telechelic PIB polymers, halide di-telechelic PIB polymers, amine di-telechelic PIB polymers, alcohol/amine di-telechelic PIB polymers, polyurethanes, and polyureas containing the residue of the low cost bifunctional initiators described above, including, but not limited to, bBCB-ol, and bBdClCB. It is believed that these compounds and polymers can be synthesized using known methods simply by substituting the low cost bifunctional initiators described above, including, but not limited to, bBCB-ol, and bBdClCB for HDCCl, on a 1 to 1 mole basis. In one or more embodiment, allyl di or tri-telechelic PIB polymers, halide di or tri-telechelic PIB polymers, amine di or tri-telechelic PIB polymers, polyurethanes, and polyureas according to various embodiments of the present invention may be synthesized as set forth in U.S. Pat. Nos. 8,552,118, 8,674,034, and 9,359,465; U.S. Published Patent Application Nos. 2013/0331538 and 2015/0191566; and International Patent Application No. WO 2010/039986, the disclosures of which are incorporated herein by reference in their entirety, by substituting the appropriate low cost bifunctional initiator (including, but not limited to, bBCB-ol and bBdClCB) and trifunctional initiator of the present invention as described above, for the initiators used therein (including but not limited to those initiators described in U.S. patent Nos. U.S. Pat. Nos. 5,733,998 and 8,889,926, the disclosure of which are incorporated herein by reference in their entirety), on a 1 to 1 mole basis.

Further while the low cost bifunctional initiators of the present invention are particularly useful in the formation of bidirectional telechelic PIB polymers, they may also be used to form bidirectional telechelic polystyrenes, polyurethane, polyurea, and structurally new di-block (e.g., PIB-Polystyrene (PSt)) and tri-block (e.g., PSt-PIB-PSt) polymers using known reaction mechanisms. In one or more embodiments, PIB-polystyrene block co-polymers according to the present invention may be synthesized as shown in Example 12, below. Accordingly, in a variety of embodiments, the present invention also includes diblock and triblock polymers comprising PIB, polyurethane, polystyrene, or polyurea blocks that contain the residue of the low cost bifunctional initiators described above, including, but not limited to, bBCB-ol and bBdClCB. It is believed that these polymers can be synthesized using known methods simply by substituting the low cost bifunctional initiators described above, including, but not limited to, bBCB-ol and bBdClCB, for HDCCl on a 1 to 1 mole basis.

Further, the polymers produced by bBCB-ol or bBdClCB, in particular, contain initiator residues that are valuable sites for further derivatizations and thus for the creation of useful new products. In various embodiments, the novel initiators of the present invention, including but not limited to bBCB-ol or bBdClCB, may be used to form PIB polymers with a variety of useful end groups, including without limitation, allyl groups, hydroxyl groups, primary or tertiary alcohols, halides, amine groups, azide groups, thiol groups, furanyl groups, alkynyl groups, cyano groups, and combinations thereof. It is believed that these polymers may be synthesized using by conventional methods by substituting a novel initiator of the claimed invention for the conventional initiator molecule. And because these molecules contain the novel initiators of the present invention, it is believed that these molecules too are novel.

Importantly, low cost bifunctional initiators of the present invention can be used to form allyl telechelic PIB polymers. As will be apparent to those of skill in the art, allyl telechelic PIB is a key intermediate for the synthesis of primary alcohol telechelic PIB (HO-PIB-OH), which is in turn the key intermediate for the preparation of PIB-based polyurethanes. The conversion of allyl telechelic PIB to HO-PIB-OH has been described (see, e.g., U.S. Pat. Nos. 8,552,118 and 9,359,465; U.S. Published Patent Application No. 2015/

0191566; and International Patent Application No. WO 2010/039986, the disclosures of which are incorporated herein by reference in their entirety), together with use of HO-PIB-OH for the synthesis of PIB-PUs. (See, e.g., U.S. Pat. Nos. 8,552,118, 8,674,034, and 9,359,465; U.S. Published Patent Application Nos. 2013/0331538 and 2015/0191566; and International Patent Application No. WO 2010/039986, the disclosures of which are incorporated herein by referenced in their entirety). The inventors are unaware, however, of any publication or patent teaching the use of 2,4,7,9-tetramethyl-tricyclo[6.2.0.0$^{3,6}$]deca-1(8),2,6-triene-4,9-diol (bBCB-ol) (XXI) or 4,9-dichloro-2,4,7,9-tetramethyl-tricyclo[6.2.0.0$^{3,6}$]deca-1(8),2,6-triene (bBdClCB) (XXIV) as cationogens for the preparation of allyl telechelic PIB or for the initiation of cationic polymerization.

Scheme 4 below outlines a route to allyl telechelic PIB starting with bBCB-ol and bBdClCB:

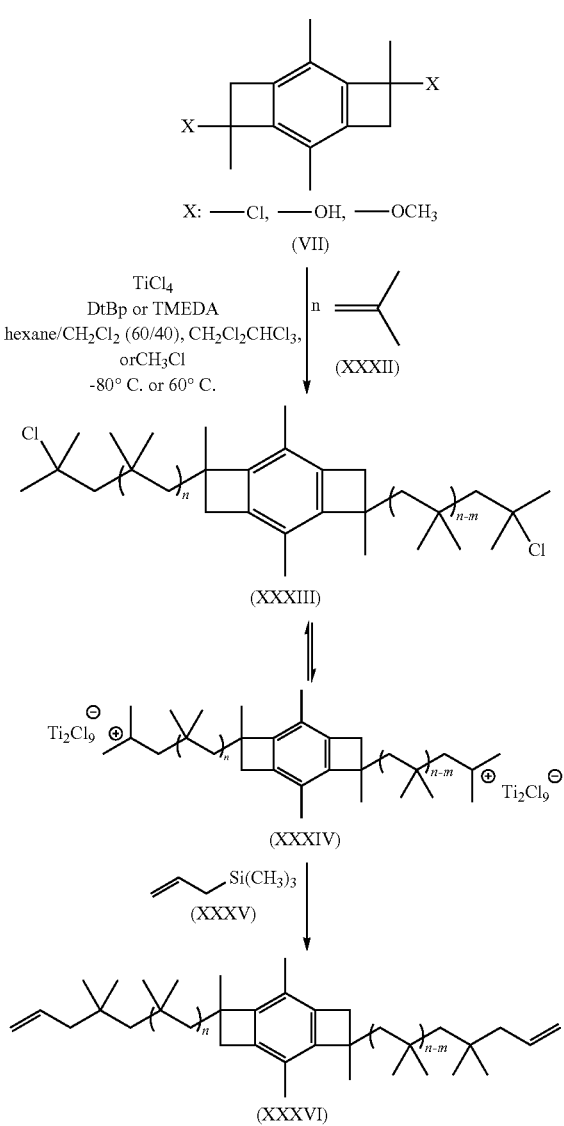

where n is the number of isobutylene molecules that react to form the PIB chains and m is the number forming one of the two PIB chains. In one or more embodiments, n is an integer from 4 to about 10,000, or from about 14 to about 9,000, or from about 20 to about 8,000, or from about 30 to about 7,000, or from about 50 to about 6,000, or from about 150 to about 5,000, or from about 200 to about 4,000, or from about 500 to about 3,000, or even from about 1,000 to about 2,000. In one or more embodiments, m is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. As will be apparent, in embodiments where the molecular weight distribution is narrow, it may be assumed that values of n and n-m are almost equal. Here, as well as elsewhere in the specification and claims, individual range limits can be combined to form alternative non-disclosed range limits. (See Examples 4 and 5, below) Except for the use of the new low cost initiator, this route to allyl telechelic PIB is identical to that used earlier with the HDCCl initiator. (See, e.g., U.S. Pat. Nos. 8,552,118, 8,674,034, and 9,359,465; U.S. Published Patent Application Nos. 2013/0331538 and 2015/0191566; and International Patent Application No. WO 2010/039986, the disclosures of which are incorporated herein by reference in their entirety).

In these embodiments, a suitable solvent or co-solvent mixture and a proton trap are combined in a suitable reaction vessel and cooled to a temperature of from about −50° C. to about −90° C. In various embodiments, suitable solvents or co-solvents combinations may include, without limitation, hexane/CH$_2$Cl$_2$ (60/40), CH$_2$Cl$_2$, CHCl$_3$, or CH$_3$Cl. In one or more embodiments, the proton trap may be DtBP, TMEDA, or DtBP with TMEDA. In some embodiments, the combination may be cooled to a temperature of from about −50° C. to about −80° C., in other embodiments, from about −50° C. to about −70° C., in other embodiments, from about −50° C. to about −60° C., in other embodiments, from about −60° C. to about −90° C., in other embodiments, from about −70° C. to about −90° C., in other embodiments, from about −80° C. to about −90° C., in other embodiments, from about −60° C. to about −90° C. and in other embodiments, from about −75° C. to about −85° C. Under strong stirring bBdClCB and/or bBCB-ol are then added to the reaction vessel and the system stirred for from about 5 min. Then isobutylene (IB) is added followed by the addition of a Friedel-Crafts acid, such as TiCl$_4$. In these embodiments, the polymerization is allowed to proceed for from 50 to 70 min before being terminated with an allyl silane such as trimethylallylsilane (ATMS) to introduce a terminal allyl group. In some of these embodiments, polymerization is allowed to proceed for from 10 to 20 min, in other embodiments, from 10 to 30 min, in other embodiments, from 10 to 40 min, in other embodiments, from about 10 to 60 min, in other embodiments, from about 10 to 70 min, in other embodiments, from about 20 to 70 min, and in other embodiments, from about 45 to 65 min, before being terminated. In some of these embodiments, the polymerization was allowed to proceed 60 min and was terminated with 2.4 mL (1.5×10$^{-2}$ mol) distilled and prechilled allyltrimethylsilane (ATMS). As will be appreciated, the ATMS serves to add the terminal allyl group to the PIB chains to form molecule (XVIII).

In some other embodiments, the chlorine terminated PIB is dehydrohalogenated to form an exo olefin group by refluxing it with potassium tertiary butoxide, as described in U.S. Pat. No. 4,342,849 to Kennedy et al., the disclosure of which in incorporated herein by reference in its entirety. In still other embodiments, in-situ quenching of quasi-living polymerization of isobutylene with 1,2,2,6,6-pentamethylpiperidine gives exo olefine terminated PIB as described in Simison, K. L., Stokes, C. D., Harrison, J. J., Storey, R. F., Macromolecules 39(7), 2481, (2006), the disclosure of which in incorporated herein by reference in its entirety.

The system is then stirred for from about 20 to 40 min before methanol is added to fully terminate the polymerization and to decompose the TiCl$_4$ and the system allowed to warm to room temperature. In some of these embodiments, the system is stirred for from 20 to 30 min, in other embodiments, from about 30 to 40 min, and in other embodiments, from about 25 to 35 min, before the methanol is added. In some of these embodiments, system is then stirred for about 30 min before the methanol is added. The resulting allyl telechelic PIB may be collected and purified using any conventional means known in the art. In some embodiments, the solution is concentrated by rotary evaporation, precipitated into methanol, the methanol was decanted, the polymer dissolved in hexane, and washed with 5% aqueous sodium bicarbonate and water. The organic phase is then dried over night over magnesium sulfate, and filtered through fine sintered glass. Finally, the solvent is evaporated by rotary evaporation and the allyl telechelic PIB, a colorless viscous mass, is dried in high vacuum.

In one or more embodiments, the allyl telechelic PIB may have the structure:

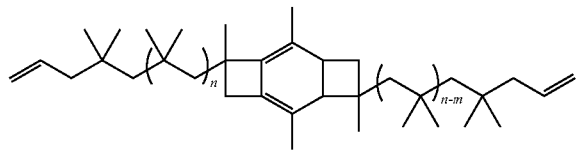

(XXXVI)

where n is an integer from 4 to about 10,000, or from about 14 to about 9,000, or from about 20 to about 8,000, or from about 30 to about 7,000, or from about 50 to about 6,000, or from about 150 to about 5,000, or from about 200 to about 4,000, or from about 500 to about 3,000, or even from about 1,000 to about 2,000. In one or more embodiments, m is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

The following equations describe further processes and compounds that can be produced via various embodiments of the present invention. As a general rule, all of the following reactions can be run at a 95% or better conversion rate.

(A) Cationic living isobutylene polymerization affords a first intermediate which is, for example, a tert-Cl-terminated PIB chain:

~~~C(CH$_3$)$_2$—[CH$_2$—C(CH$_3$)$_2$]$_n$—CH$_2$—C(CH$_3$)$_2$—Cl (A)

where ~~~ represents the remaining portion of a one, two, or three arm molecule containing a residue of one of the low cost initiators of the present invention as described above and n is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

As would be apparent to those of skill in the art, ~~~ can in some instances represent another chlorine atom in order to permit the production of substantially linear di-terminal primary alcohol PIBs or two other chlorine atoms in order to permit the production of star shaped tri-terminal primary alcohol PIBs using this method. As will be appreciated by those of skill in the art, all of the PIB chains are formed substantially simultaneously. Additionally, it should be noted that the present invention is not limited to the above specific linking groups (i.e., the —C(CH$_3$)$_2$) between the repeating PIB units and the remainder of the molecules of the present invention.

The next step is the dehydrchlorination of (A) to afford the second intermediate shown below:

~~~C(CH$_3$)$_2$—[CH$_2$—C(CH$_3$)$_2$]$_n$—CH$_2$—C(CH$_3$)=CH$_2$ (B).

The dehydrochlorination of (A) may be accomplished according to any method known in the art for that purpose. In some embodiments, the chlorine terminated PIB may be dehydrohalogenated to form exo olefin group by refluxing 20 hours with potassium tertiary butoxide, cooling, water washing repeatedly, and drying as shown in U.S. Pat. No. 4,342,849 to Kennedy, the disclosure of which is incorporated herein by reference in its entirety, and shown in Scheme 5 below Scheme 5

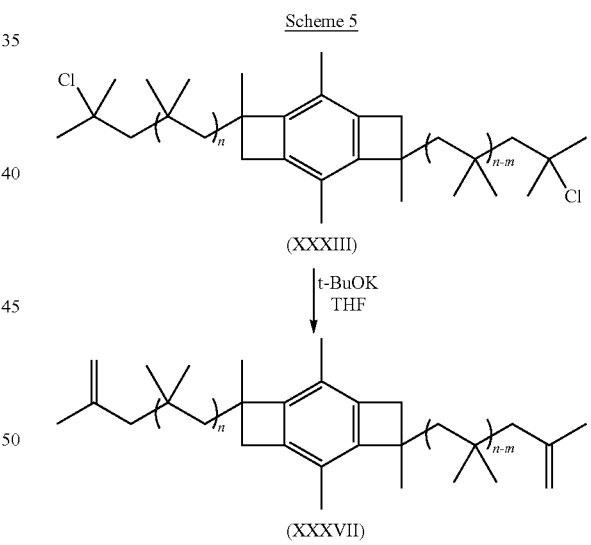

(XXXIII)

t-BuOK
THF (XXXVII)

where n is an integer from 4 to about 10,000, or from about 14 to about 9,000, or from about 20 to about 8,000, or from about 30 to about 7,000, or from about 50 to about 6,000, or from about 150 to about 5,000, or from about 200 to about 4,000, or from about 500 to about 3,000, or even from about 1,000 to about 2,000. In one or more embodiments, m is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

The third step is the anti-Markovnikov hydrobromination of (B) to afford the primary bromide shown below:

~~~C(CH3)2-[CH2-C(CH3)2]$_n$-CH2-CH(CH3)-CH2-Br (C).

The hydrobromination of (B) may be accomplished according to any method known in the art for that purpose provided. In some embodiments, hydrobromination of (B) may be accomplished by bubbling first air for 30 minutes and then HBr gas through a solution containing (B) for 10 minutes as known in the art for that purpose. In some embodiments, the (B) may be hydrobromated as shown in Scheme 6.

Scheme 6

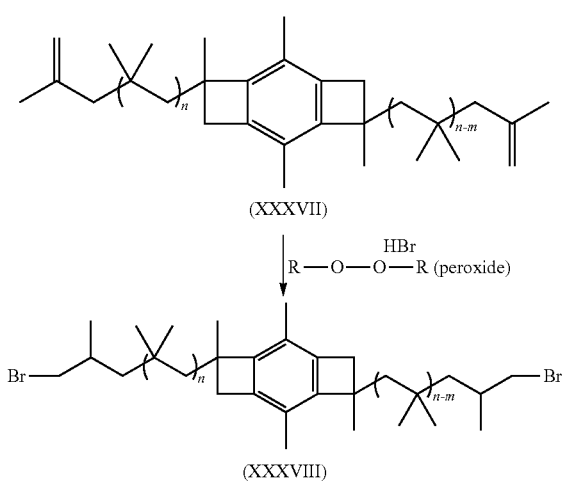

(XXXVII)

HBr
R—O—O—R (peroxide)

(XXXVIII)

where n and m are as set forth above.

The fourth step is the conversion of the primary bromide by the use of a base NaOH, KOH, or tert-BuONa) as shown in Scheme 7 below to a primary hydroxyl group according to the following formula:

~~~C(CH$_3$)$_2$—[CH$_2$—C(CH$_3$)$_2$]$_n$—CH$_2$—CH(CH$_3$)—CH$_2$—OH (D).

The conversion of the primary bromide of (C) to a primary hydroxyl group may be accomplished according to any method known in the art for that purpose. In some embodiments, conversion of the primary bromide of (C) to a primary hydroxyl group may be accomplished by nucleophilic substitution on the bromine with the addition of an aqueous solution of NaOH. Optionally, a phase transfer catalyst such as tetraethyl ammonium bromide can be added to speed up the reaction.

Scheme 7

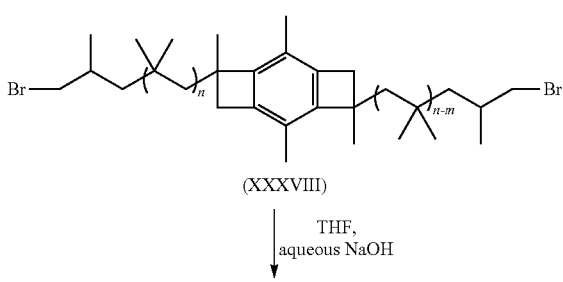

(XXXVIII)

THF, aqueous NaOH

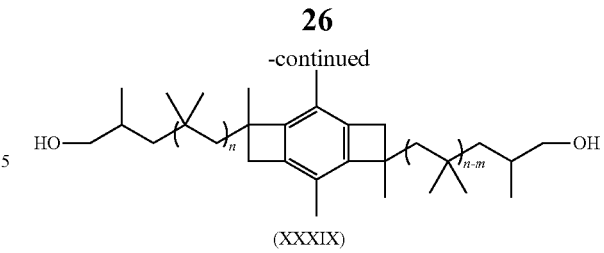

(XXXIX)

where n and m are as set forth above.

In another embodiments, the following reaction steps can be used to produce a primary alcohol-terminated PIB compound according to the present invention.

Instead of the dehydrochlorination, as outlined in (B) above, one can use an allyl silane such as trimethyl allyl silane to prepare an allyl terminated PIB (See e.g., Scheme 4, above):

~~~C(CH$_3$)$_2$—[CH$_2$—C(CH$_3$)$_2$]$_n$—CH$_2$—CH=CH$_2$ (B').

Suitable allyl silanes may include, without limitation, trimethyl allyl silane.

Similarly to the reaction shown in (C) above, the (B') intermediate is converted to the primary bromide by an anti-Markovnikov reaction (hydrobromination of the terminal allyl groups) to yield the following compound:

~~~C(CH$_3$)$_2$—[CH$_2$—C(CH$_3$)$_2$]$_n$—CH$_2$—CH$_2$—CH$_2$—Br (C').

(C') can be converted to a primary alcohol-terminated compound as discussed above to yield the following compound:

~~~C(CH$_3$)$_2$—[CH$_2$—C(CH$_3$)$_2$]$_n$—CH$_2$—CH$_2$—CH$_2$—OH (D').

In still other embodiments, bis-hydroxy telechelic PIB according to the present invention may be made according to the two step reaction shown in Scheme 8.

Scheme 8

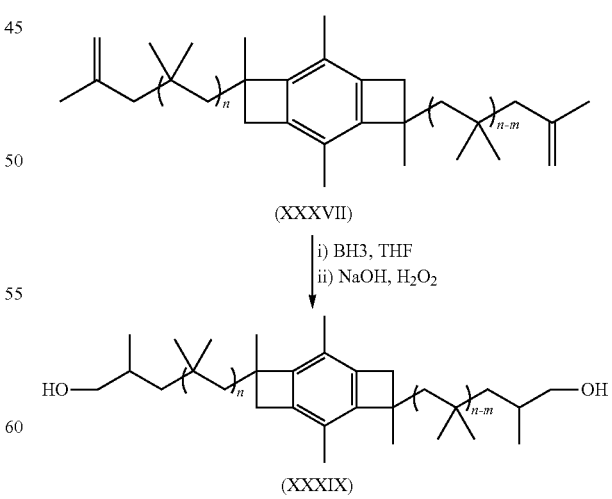

(XXXVII)

i) BH3, THF
ii) NaOH, H$_2$O$_2$ (XXXIX)

where n and m are as set forth above. In one or more embodiments, the alcohol di-telechelic PIB may have the structure:

(XI)

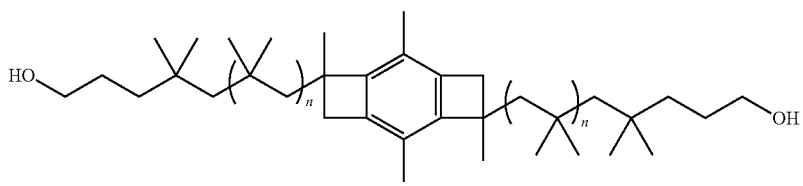

where each individual n is an integer from 2 to about 5,000, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

In one embodiment, the primary alcohols that can be used as terminating groups in the present invention include, but are not limited to, any straight or branched chain primary alcohol substituent group having from 1 to about 12 carbon atoms, or from 1 to about 10 carbon atoms, or from 1 to about 8, or from about 1 to about 6 carbon atoms, or even from about 2 to about 5 carbon atoms. Here, as well as elsewhere in the specification and claims, individual range limits can be combined to form alternative non-disclosed range limits.

In some other embodiments, low cost bifunctional initiators of the present invention may also be used to form novel amine terminated PIB polymers. In one or more embodiments, the novel amine terminated PIB polymers may have the following formula:

(XII)

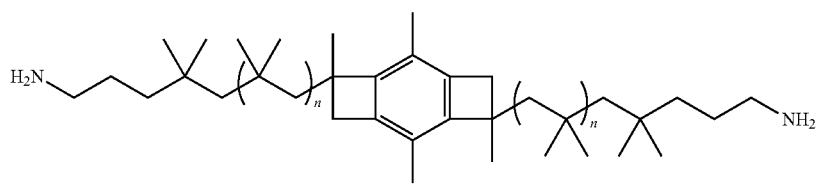

wherein each n is an integer from 2 to about 5,000. In some embodiments, each n may be an integer from 2 to about 4,500, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. Here, as well as elsewhere in the specification and claims, individual range limits can be combined to form alternative non-disclosed range limits.

These novel amine terminated PIB polymers may be formed using any known method wherein the novel initiator of the present invention described above is substituted for the initiator ordinarily used. These novel amine terminated PIB polymers may be formed according to any of the methods for doing so described in U.S. Pat. Nos. 8,552,118 and 9,359,465, the disclosures of which are incorporated herein by reference in their entirety, where one of the novel initiator of the present invention is substituted for the HDCCl initiator. In some embodiments, novel amine terminated PIB polymers of the present invention may be made as set forth in Scheme 9 below;

Scheme 9

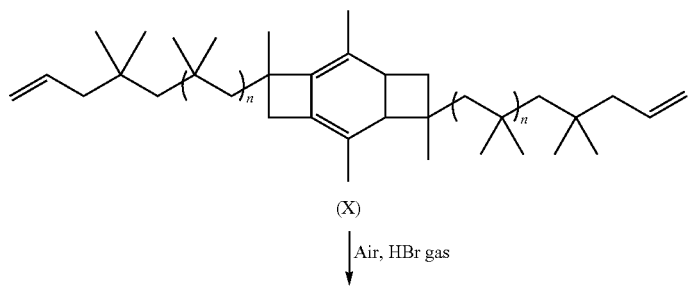

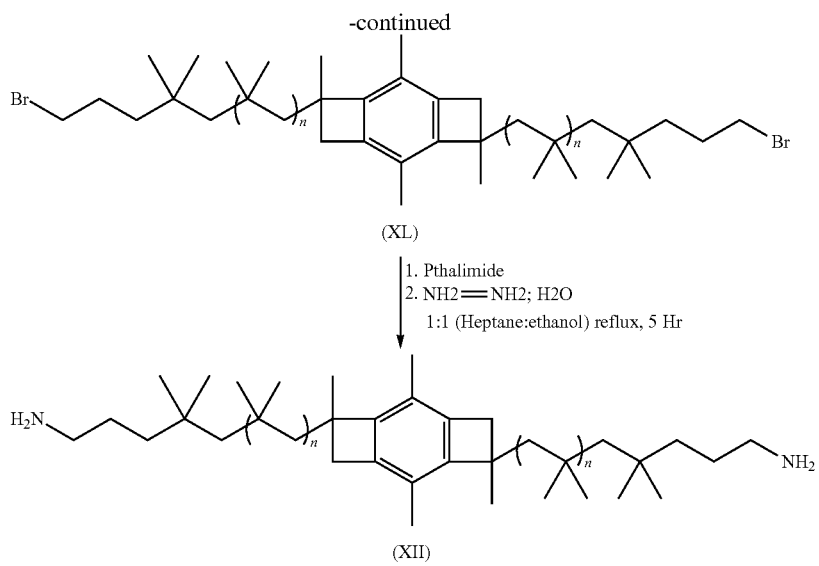

(XL)

1. Pthalimide
2. NH2=NH2; H2O
   1:1 (Heptane:ethanol) reflux, 5 Hr (XII)

In these embodiments, allyl terminated PIB (X) is converted to the novel amine terminated PIB (XII) polymer in three steps: (a) hydrobromation of the allyl terminated PIB (X) with HBr gas as described above to produce the terminal primary bromine terminated PIB (XL); (b) substitution of the terminal primary bromine to phthalimide-terminated polyisobutylene (PIB-(CH$_2$)$_3$-phthalimide) by reacting it with potassium pthalimide; and (c) hydrazinolysis of the phthalimide terminated polyisobutylene to primary amine-terminated polyisobutylene (XII).

In various embodiments, synthesis of a phthalimide-terminated polyisobutylene may be carried out according to Scheme 10 shown below:

Scheme 10

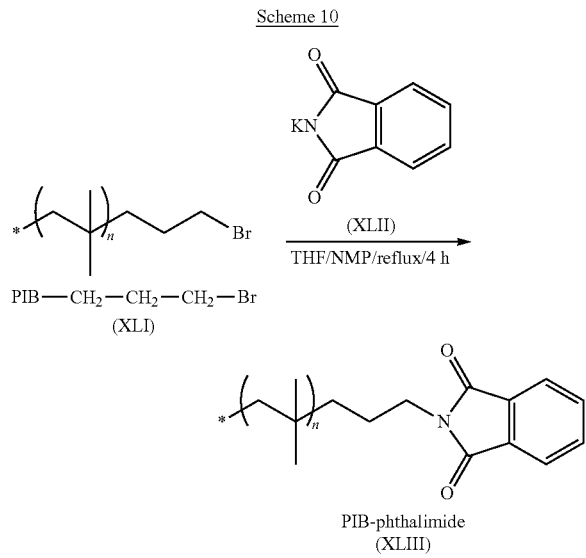

where * is the remainder of the molecule and n is an integer from 2 to about 5000.

In one or more of these embodiments, the bromine terminated PIB (XLI) is dissolved in a suitable solvent such as THF and N-methyl-2-pyrrolidone (NMP) is added to increase the polarity of the medium. Potassium phthalimide (XLII) is then added to the solution and it is refluxed at a temperature of from about 70° C. to about 90° C. for from about 3 to 5 hours. The reaction mixture is then diluted by the addition of hexane and washed with excess water. The organic layer is separated, washed three with distilled water, and dried over MgSO$_4$. The hexane is removed by a rotory evaporation (rotovap), and the resulting phthalimide terminated PIB polymer (XLIII) is dried under vacuum.

In one or more embodiments, synthesis of an amine-terminated PIB (XLIV) from the phthalimide terminated PIB (XLIII) may be carried out according Scheme 11 shown below:

Scheme 11

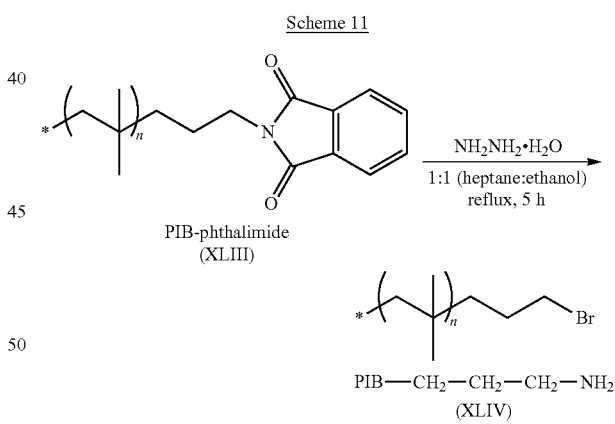

where * is the remainder of the molecule and n is an integer from 2 to about 5000. In some of these embodiments, the phthalimide terminated PIB (XLIII) is dissolved in a mixture of heptane and ethanol, and hydrazine hydrate is added. This mixture is then refluxed at from about 100° C. to about 110° C. for about 4-6 hours. The charge is the diluted with hexane and washed with excess water. The organic layer is then separated, washed with distilled water. and dried over MgSO$_4$. The hexane is removed by a rotory evaporation (rotovap), and the resulting amine terminated PIB (XLIV) polymer is dried under vacuum.

As noted above, the primary alcohol-terminated PIBs are useful intermediates in the preparation of polyurethanes by reaction via conventional techniques, i.e., by the use of known isocyanates, including but not limited to 4,4'-methylenediphenyl diisocyanate, (MDI) and 4,4'-methylene dicyclohexyl diisocyanate (HMDI), known chain extension agents including, but not limited to 1,4-butane diol (BDO), 1,6-hexane diol (HDO) and/or 1,6-hexane diamine (HDA), and a catalyst. As set forth above, polyurethanes according to various embodiments of the present invention may be synthesized as set forth in U.S. Pat. Nos. 8,552,118, 8,674, 034, and 9,359,465, the disclosures of which are incorporated herein by reference in their entirety, by substituting the appropriate low cost bifunctional initiator (including, but not limited to, bBCB-ol and bBdClCB) of the present invention as described above, for the initiators used therein on a 1 to 1 mole basis.

A great advantage of these polyurethanes (PUs) is their outstanding hydrolytic and oxidative and biological stability imparted by the stable PIB segment. Moreover, since PIB is known to be biocompatible, any PU made from the PIB compounds of the present invention is novel as well as biocompatible.

In one or more embodiments, the PIB polyurethane comprising the residue of the novel low cost difunctional initiator of the present invention may have the structure:

In one or more of these embodiments, each n may be an integer in the range of from 2 to about 4,500, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. In one or more embodiments, each m may be an integer from 2 to 900,000, in other embodiments, from 2 to 700,000, in other embodiments, from 2 to 500,000, in other embodiments, from 2 to 400,000 in other embodiments, from 2 to 200,000, in other embodiments, from 100 to 1,000,000, in other embodiments, from 1000 to 1,000,000, in other embodiments, from 10,000 to 1,000,000, in other embodiments, from 100,000 to 1,000,000, in other embodiments, from 300,000 to 1,00,000, and in other embodiments, from 500,000 to 1,000,000. Here, as well as elsewhere in the specification and claims, individual range limits can be combined to form alternative non-disclosed range limits.

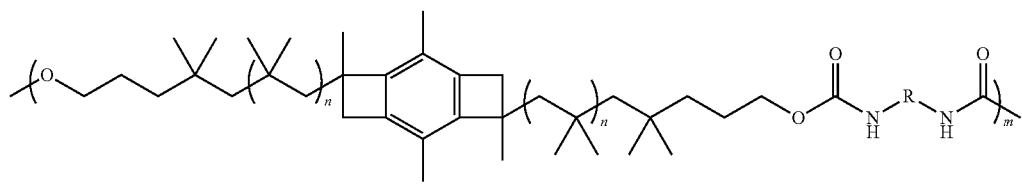

(XIII)

where each n is an integer from 2 to about 5,000; m is an inter from 2 to about 1,000,000; and R is the residue of a diisocyanate. In various embodiments, R may be the residue of toluene diisocyanate or 4, 4'-diphenylmethane diisocyanate. In some embodiments, R may the formula:

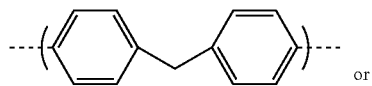

(XIV)

or

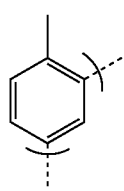

(XV)

As also noted above, the amine-terminated PIBs are useful intermediates in the preparation of polyureas by reaction via conventional techniques, i.e., by the use of known isocyanates, including but not limited to 4,4'-methylenediphenyl diisocyanate, (MDI) and 4,4'-methylene dicyclohexyl diisocyanate (HMDI). As set forth above, polyurea according to various embodiments of the present invention may be synthesized as set forth in U.S. Pat. Nos. 8,552,118, and 9,359,465, the disclosures of which are incorporated herein by reference in their entirety, by substituting the appropriate low cost bifunctional initiator (including, but not limited to, bBCB-ol and bBdClCB) of the present invention as described above, for the initiators used therein on a 1 to 1 mole basis.

In one or more embodiments, the present invention is directed to a PIB based polyuria comprising the residue of the novel low cost difunctional initiator of the present invention may have the structure:

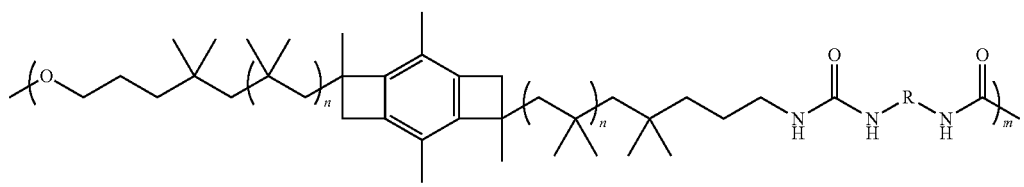

(XVI)

where each n is an integer from 2 to about 5,000; m is an inter from 1 to about 1,000,000; and R is the residue of a diisocyanate. In various embodiments, R may be the residue of toluene diisocyanate or 4, 4'-diphenylmethane diisocyanate. In some embodiments, R may the formula:

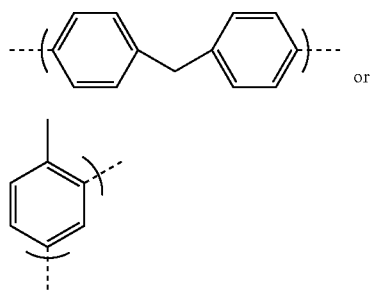

In one or more of these embodiments, each n may be an integer in the range of from 2 to about 4,500, or from about 7 to about 4,500, or from about 10 to about 4,000, or from about 15 to about 3,500, or from about 25 to about 3,000, or from about 75 to about 2,500, or from about 100 to about 2,000, or from about 250 to about 1,500, or even from about 500 to about 1,000. In one or more embodiments, each m may be an integer from 2 to 900,000, in other embodiments, from 2 to 700,000, in other embodiments, from 2 to 500,000, in other embodiments, from 2 to 400,000 in other embodiments, from 2 to 200,000, in other embodiments, from 100 to 1,000,000, in other embodiments, from 1000 to 1,000,000, in other embodiments, from 10,000 to 1,000,000, in other embodiments, from 100,000 to 1,000,000, in other embodiments, from 300,000 to 1,00,000, and in other embodiments, from 500,000 to 1,000,000. Here, as well as elsewhere in the specification and claims, individual range limits can be combined to form alternative non-disclosed range limits.

As will be apparent, primary alcohol-terminated PIBs and amine-terminated PIBs of various embodiments of the present invention are also useful intermediates in the formation of polyurethane ureas by reaction via conventional techniques by substituting the appropriate low cost bifunctional initiator (including, but not limited to, bBCB-ol and bBd-ClCB) of the present invention as described above, for the initiators used therein on a 1 to 1 mole basis. In one or more embodiments, the polyurethane ureas according to the present invention may be made using the methods described in U.S. Published Application Number 1023/033,538, U.S. Published Application Number 2015/0191566, U.S. Published Application Number 2011/0213084, and U.S. Pat. No. 8,674,034, all of which are incorporated herein by reference.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Synthesis of Diacetyl Durene (DAD)

Friedel-Crafts diacylation of durene was carried out by a procedure described in the literature with acetyl chloride (AcCl) in the presence of aluminum chloride ($AlCl_3$) and $CS_2$ solvent (Pinkus A. G., Kalyanam N., *Organic Preparations and Procedures Int,* 10 (6), 255, 1978). The ratio of $AlCl_3$/AcCl/durene we used was approximately 6:3:1.

Thus, in a 500 mL round bottom flask equipped with a condenser, mechanical stirrer, and three-way valve, under a nitrogen atmosphere, were placed AcCl (13 g, 0.16 moles), $AlCl_3$ (34 g, 0.25 moles), and 70 mL dry $CS_2$ (in this sequence), the system was heated to reflux and stirred for ~8 hrs. To the refluxing stirred solution was slowly added durene (5 g, 0.037 moles) dissolved in 50 mL $CS_2$, and stirring was continued at reflux overnight. That reaction was taking place was indicated by the originally yellow solution turning red. Then the content of the flask was poured onto crushed ice, and the system was acidified by dropwise addition of concentrated aqueous hydrochloric acid. Methylene chloride (~100 mL) was added and the aqueous and organic phases were separated. The aqueous phase was washed twice with ~60 mL portions of methylene chloride, and the washings were combined with the organic phase. Then the organic phase was washed with aqueous sodium carbonate (10%), distilled water, and dried over anhydrous sodium sulfate for ~2 hrs. The solvent was removed by rotary evaporation and the white solid was recrystallized from benzene. Yield 90% of DAD. Mp 177° C. FIG. 1 shows the $^1$H NMR spectrum of DAD. $H^1$NMR ($CDCl_3$): =2.08 ppm (s, 12H, a), δ=2.44 ppm (s, 6H, b).

Example 2

Synthesis of 2,4,7,9-tetramethyl-tricyclo[$6.2.0.0^{3,6}$] deca-1(8),2,6-triene-4,9-diol (bBCB-ol)

Figure 3:
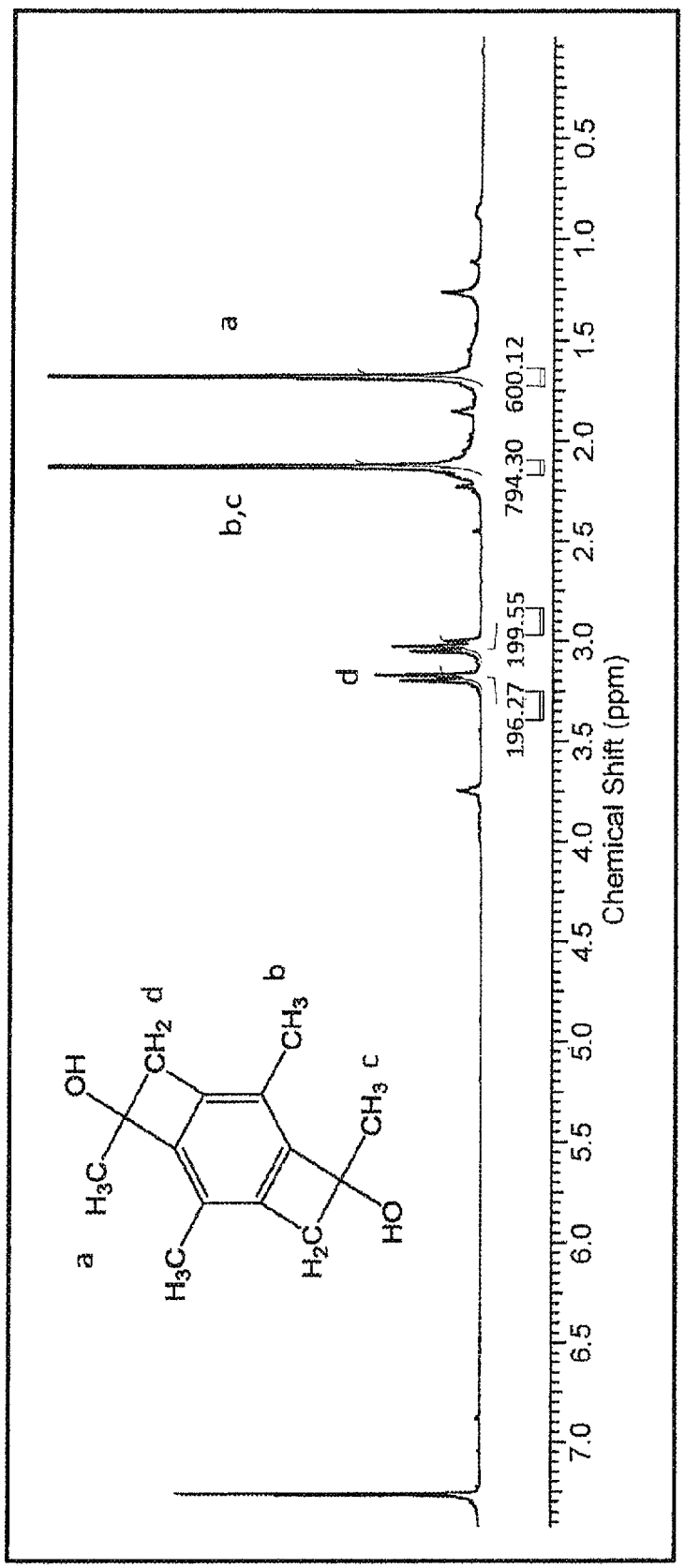
FIG. 3 is a $^1$H NMR spectrum of bBCB-ol.

A 300 mL Pyrex flask equipped with a magnetic stir bar and reflux condenser, containing diacetyl durene in benzene solution (7.45×10$^{-3}$M) under a nitrogen atmosphere was placed in a UV chamber. The solution was stirred and irradiated with six 9 W, 300 nm broad band UV lamps (Philips UVB Broad Band PL-S 9 W/12) for 72 hrs at 50° C., using the apparatus shown in FIG. 2. Subsequently, the solvent was evaporated, and the bBCB-ol, a white solid, was characterized by $^1$H NMR spectroscopy (FIG. 3). $H^1$NMR ($CDCl_3$): δ=1.67 ppm (s, 6H, a), 8=2.14 ppm (s, 6H, b), 8=2.13 ppm (s, 2H, c), 8=3.02, 3.05, 3.17, 3.20 ppm (s, 4H, d)

Example 3

Figure 5:
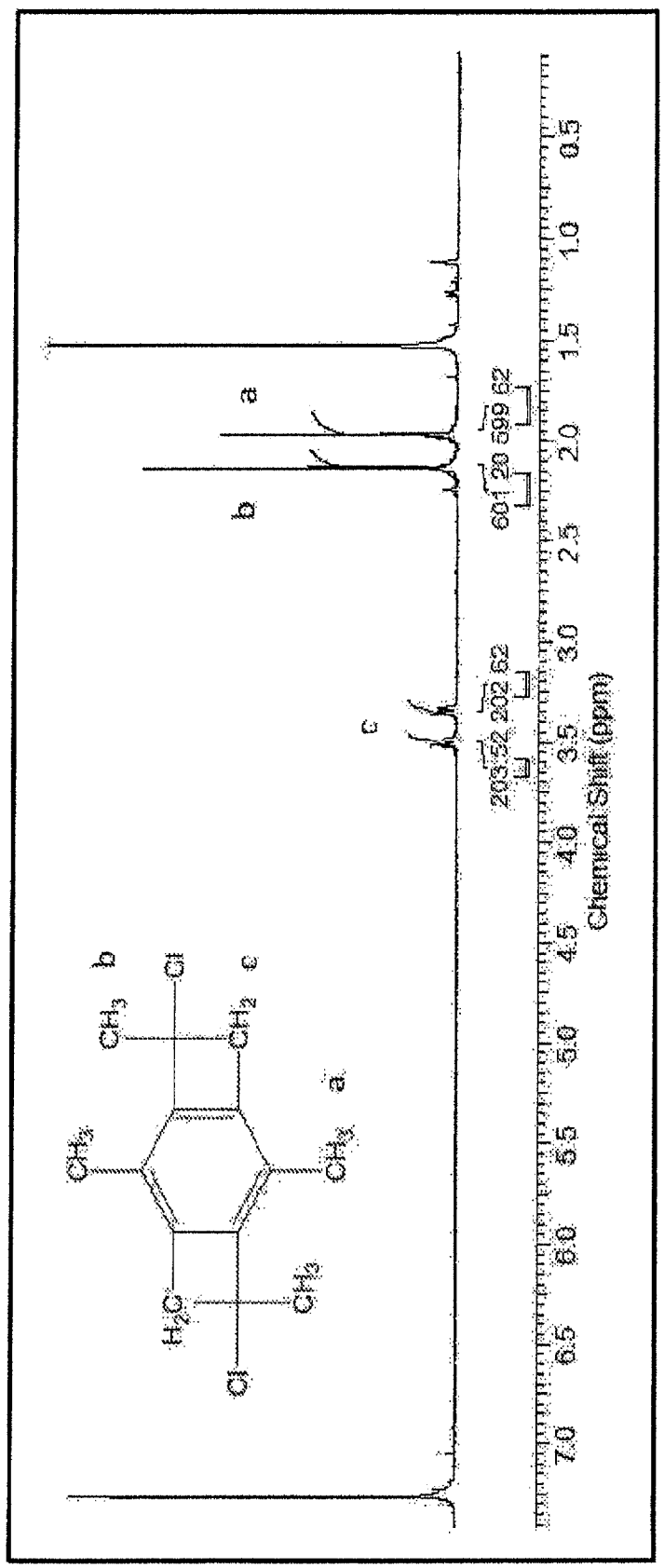
FIG. 5 is a $^1$H NMR spectrum of bBdClCB.

Synthesis of 4,9-dichloro-2,4,7,9-tetramethyl-tricyclo [$6.2.0.0^{3,6}$]deca-1(8),2,6-triene (bBdClCB)

bBCB-ol was chlorinated using the apparatus shown in FIG. 4. bBCB-ol (0.1 g, 7×10$^{-4}$ moles) in a Schlenk flask was dissolved in methylene chloride (50 mL) under a nitrogen atmosphere and the solution was transferred by stainless steel capillary into a flame dried 100 mL tubular reactor containing CaCl$_2$. Gaseous HCl (generated by drop-wise addition of sulfuric acid onto NaCl) was bubbled into the solution by Teflon capillary tubing for six hours at 0° C. under continuous nitrogen flush. Excess HCl was neutralized by letting the gas through aqueous sodium hydroxide (See FIG. 4). The CaCl$_2$ was filtered off using a fine sintered glass filter, the solution was concentrated by rotary evaporation, diluted with 50 mL diethyl ether, and washed with 5% aqueous sodium bicarbonate and water. The diethyl ether layer was separated, dried over MgSO$_4$, the drying agent was filtered off, and the solvents were removed under reduced pressure. The bBdClCB, a white solid, was stored under nitrogen at −20° C. FIG. 5 shows the $^1$H NMR spectrum of bBdClCB. H$^1$NMR (CDCl$_3$): δ=1.97 ppm (s, 6H, a), 6=2.13 ppm (s, 6H, b), 6=3.33 ppm, 3.36 ppm, 3.48 ppm, 3.51 ppm (s, 2H, c)

Example 4

Synthesis of Allyl Telechelic PIB with bBdClCB

The synthesis of allyl telechelic PIB was carried out by the well-established procedure for the synthesis of telechelic PIBs (Ivan, B., Kennedy, J. P. Polym. Mater. Sci. 58, 866 (1988); Ivan, B., Kennedy, J. P. J. Polym. Sci., Part A: Polym. Chem. 28, 89 (1990)), except we used the novel initiator bBdClCB in place of HDCCl.

Thus, into a 300 mL round bottom flask equipped with a magnetic stirrer was placed 30 mL dried and distilled hexane, 20 mL dried and distilled dichloromethane and DtBP (5.0×10$^{-5}$ mol) proton trap and cooled to −80° C. Under strong stirring 7.7×10$^{-2}$ g (3.0×10$^{-4}$ mol) bBdClCB was added and the system stirred for 5 min. Then 4.6 mL (5.3×10$^{-2}$ mol) IB was added followed by the addition of 0.7 mL (6.0×10$^{-3}$ mol) TiCl$_4$. The polymerization was allowed to proceed 60 min and was terminated with 2.4 mL (1.5×10$^{-2}$ mol) distilled and prechilled allyltrimethylsilane (ATMS). After 30 min of stirring ~5 mL methanol was added to terminate the polymerization and to decompose the TiCl$_4$. The reactor was removed from the cooling bath and allowed to warm to room temperature. The solution was concentrated by rotary evaporation, precipitated into ~100 mL methanol, the methanol was decanted, the polymer dissolved in hexane, and washed with 5% aqueous sodium bicarbonate and water. The organic phase was dried over night over magnesium sulfate, and filtered through fine sintered glass. Finally, the solvent was evaporated by rotary evaporation and the allyl telechelic PIB, a colorless viscous mass, was dried in high vacuum.

Figure 6:
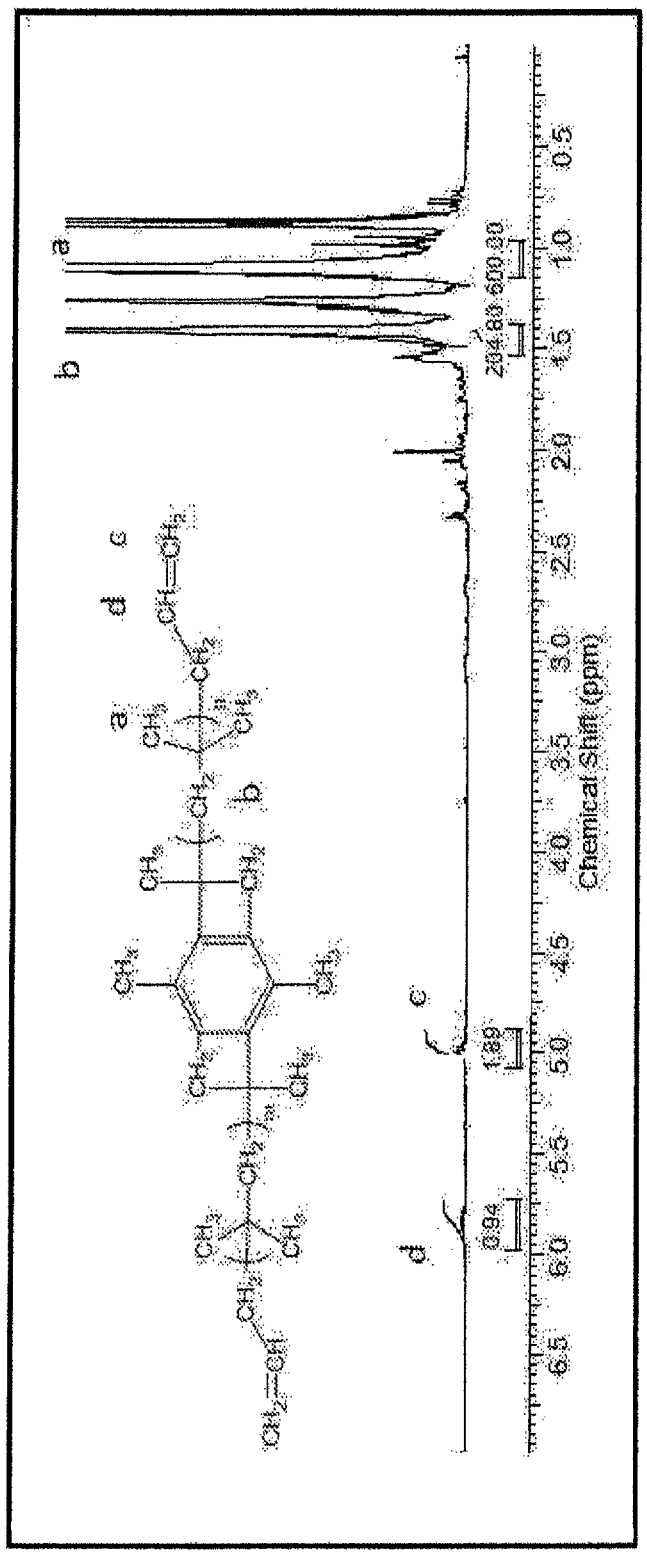
FIG. 6 is a $^1$H NMR spectrum of allyl telechelic PIB made using a novel low cost initiator according to one or more embodiments of the present invention.
Figure 7:
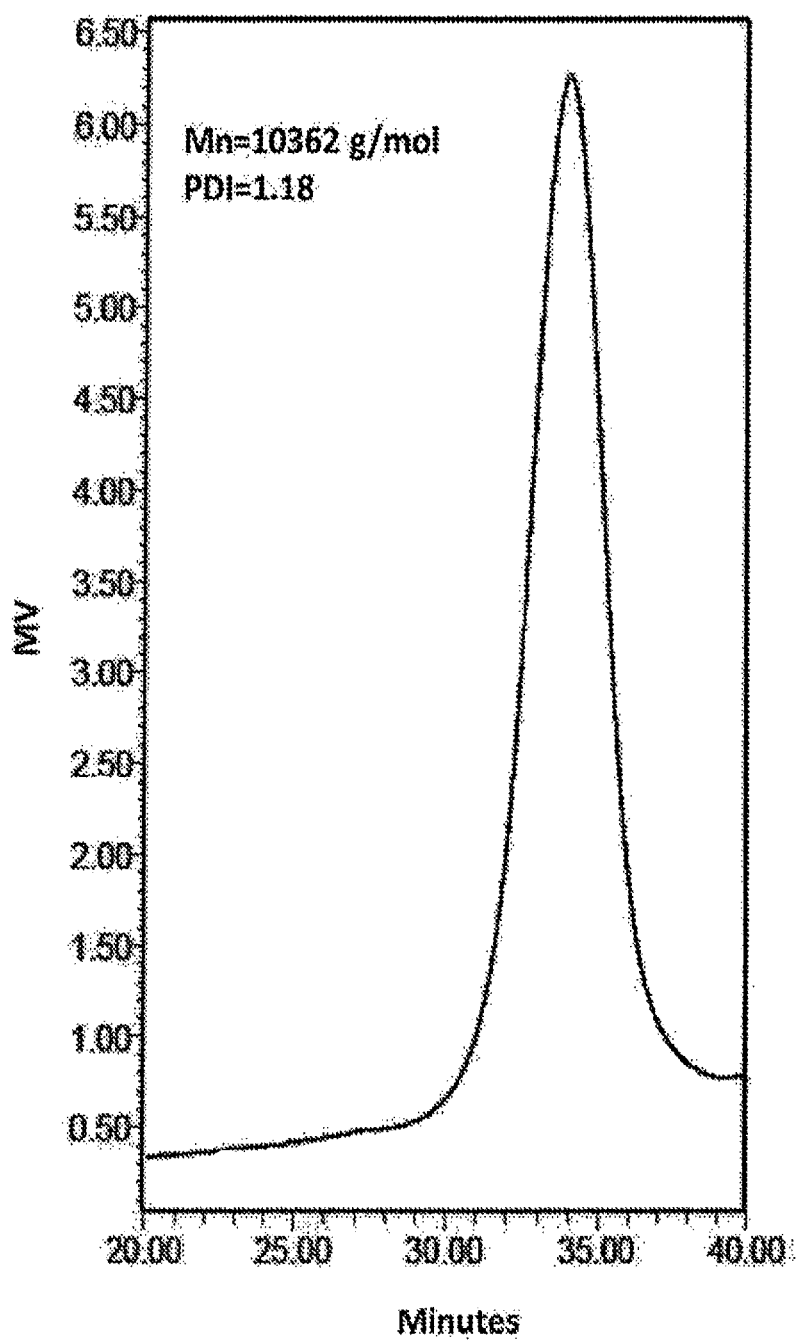
FIG. 7 is a GPC trace of allyl telechelic PIB synthesized with bBdClCB.

The allyl telechelic PIB was characterized by $^1$H NMR spectroscopy and GPC (FIGS. 6 and 7, respectively). $^1$H NMR (CDCl$_3$): δ=1.03-1.22 ppm (br, 6H, a), 1.35-1.46 ppm (br, 2H, b), 5.6-6.0 ppm (br, H, c), 4.75-5.20 ppm (br, 2H, d); Mn$_{1H\ NMR}$=11 850 g/mol. (FIG. 6). Mn$_{1H\ NMR}$ was calculated from the integrals of backbone methyl protons (—C(CH$_3$)$_2$—, δ 1.03-1.22) relative to the methylene protons or methine proton of the allyl group (=CH—, δ 4.80-5.15, and =CH$_2$, δ 5.70-6.00). According to GPC, Mn$_{GPC}$=10,360 g/mol (polystyrene standards) and Mw/Mn=1.18 (FIG. 7).

Example 5

Synthesis of Allyl Telechelic PIB with bBCB-ol

Thus, into a 500 mL round bottom flask equipped with a magnetic stirrer was placed 60 mL dried and distilled hexane, 40 mL dried and distilled dichloromethane and DtBP (1.0×10$^{-4}$ mol) proton trap and cooled to −80° C. Under strong stirring 9.2×10$^{-2}$ g (4.2×10$^{-4}$ mol) bBCB-ol was added and the system stirred for 5 min. Then 3.7 mL (4.3×10$^{-2}$ mol) IB was added followed by the addition of 1.1 mL (1.0×10$^{-2}$ mol) TiCl$_4$. The polymerization was allowed to proceed 60 min and terminated with 2.4 mL (1.5×10$^{-2}$ mol) distilled and prechilled allyltrimethylsilane (ATMS). After 30 min of stirring ~5 mL methanol was added to terminate the polymerization and decompose the TiCl$_4$. The reactor was removed from the cooling bath and allowed to warm to room temperature. The solution was concentrated by rotary evaporation, precipitated into ~100 mL methanol, the methanol was decanted, the polymer dissolved in hexane, and washed with 5% aqueous sodium bicarbonate and water. The organic phase was dried over night over magnesium sulfate, and filtered through fine sintered glass. Finally, the solvent was evaporated by rotary evaporation and the allyl telechelic PIB, a colorless viscous mass, was dried in high vacuum.

Figure 8:
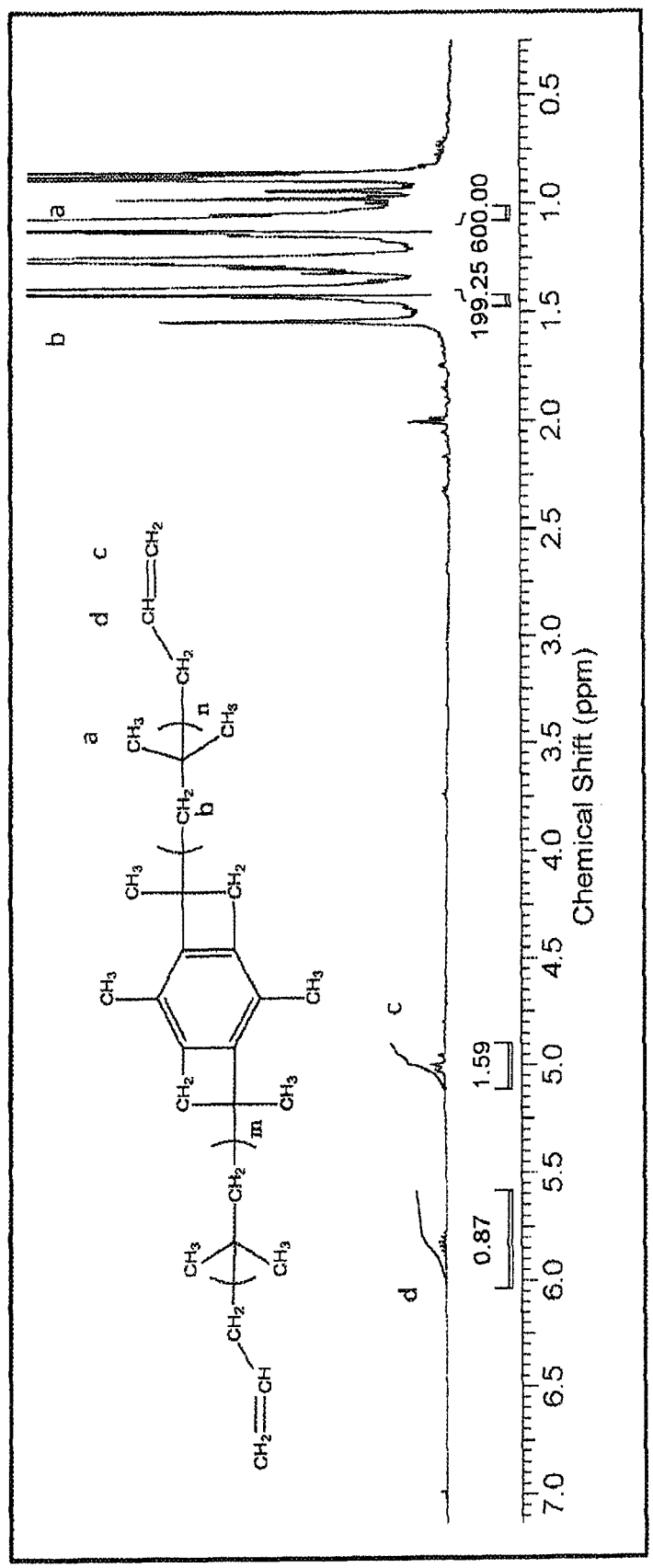
FIG. 8 is a $^1$H NMR spectrum of allyl telechelic PIB synthesized with bBCB-ol.
Figure 9:
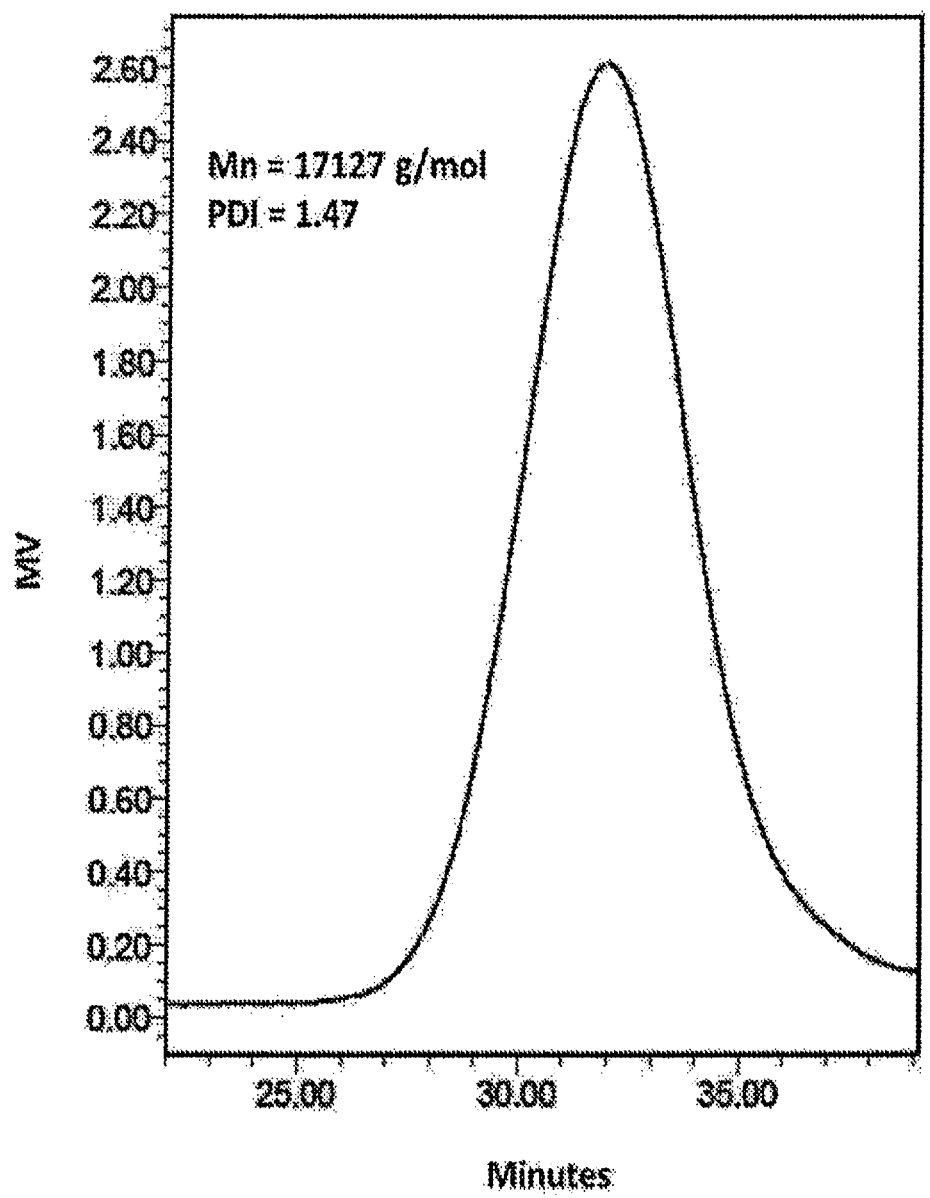
FIG. 9 is a GPC trace of allyl telechelic PIB synthesized with bBCB-ol

The allyl telechelic PIB was characterized by $^1$H NMR spectroscopy and GPC (FIGS. 8 and 9, respectively). $^1$H NMR (CDCl$_3$): δ=1.03-1.22 ppm (br, 6H, a), 1.35-1.46 ppm (br, 2H, b), 5.6-6.0 ppm (br, H, c), 4.75-5.20 ppm (br, 2H, d); Mn$_{1H\ NMR}$=15,034 g/mol. Mn$_{1H\ NMR}$ was calculated from the integrals of backbone methyl protons (—C(CH$_3$)$_2$—, δ 1.03-1.22) relative to the methylene protons or methine proton of the allyl group (=CH—, δ 4.80-5.15, and =CH$_2$, δ 5.70-6.00). (See, FIG. 8). According to GPC, Mn$_{GPC}$=17,127 g/mol (polystyrene standards) and Mw/Mn=1.47 (See, FIG. 9).

Example 6

Preparation of a Star Molecule with Three Allyl-Terminated PIB Arms (Ø-(PIB-Allyl)$_3$)

The synthesis of Ø-(PIB-Allyl)$_3$ following the procedure described by Lech Wilczek and Joseph P. Kennedy in The Journal of Polymer Science: Part A: Polymer Chemistry, 25, pp. 3255 through 3265 (1987), the disclosure of which is incorporated by reference herein in its entirety, with the substitution of a trifunctional initiator according to the present invention and as described above. The first step involves the polymerization of isobutylene to a trifunctional initiator/TiCl$_4$ system under a blanket of N$_2$ in a dry-box. Next, in a 500 mL three-neck round bottom glass flask, equipped with an overhead stirrer, the following are added: a mixed solvent (n-hexane/methyl chloride, 60/40 v/v), 2,6-di-t-butyl pyridine (0.007 M), 1,3,5-tri(2-methoxyisopropyl)benzene (0.044M), and isobutylene (2 M) at a temperature of −76° C. Polymerization is induced by the rapid addition of TiCl$_4$ (0.15 M) to the stirred charge. After 10 minutes of stirring the reaction is terminated by the addition of a 3 fold molar excess of allyltrimethylsilane (AllylSiMe$_3$) relative to the tert-chlorine end groups of the Ø-(PIB-Cl)$_3$ that formed. After 60 minutes of further stirring at −76° C., the system is deactivated by introducing a few milliliters of aqueous NaHCO$_3$, and the (allyl-terminated polyisobutylene) product is isolated.

Example 7

Preparation of Ø-(PIB-CH$_2$—CH$_2$—CH$_2$—Br)$_3$ Anti-Markovnikov Addition of HBr to Ø-(PIB-Allyl)$_3$ A 100 mL three-neck flask is charged with heptane (50 mL) and the allyl-telechelic polyisobutylene (10 grams)

formed in Example 6, above and containing the residue of a trifunctional initiator according to the present invention and as described above. Air is then bubbled through the solution for 30 minutes at 100° C. to activate the allylic end groups. Then the solution is cooled to approximately −10° C. and HBr gas is bubbled through the system for 10 minutes.

Dry HBr is generated by the reaction of aqueous (47%) hydrogen bromide and sulfuric acid (95 to 98%). After neutralizing the solution with aqueous $NaHCO_3$ (10%), the product is washed 3 times with water. Finally the solution is dried over magnesium sulfate for at least 12 hours (i.e., overnight) and filtered. The solvent is then removed via a rotary evaporator to produce the Ø-(PIB-$CH_2$—$CH_2$—$CH_2$—Br)$_3$ polymer containing the residue of a trifunctional initiator according to the present invention and as described above.

Example 8

Preparation of Ø-(PIB-$CH_2$—$CH_2$—$CH_2$—OH)$_3$ from Ø-(PIB-$CH_2$—$CH_2$—$CH_2$—Br)$_3$ The conversion of the terminal bromine product to a terminal primary hydroxyl group is performed by nucleophilic substitution on the bromine. A round bottom flask equipped with a stirrer is charged with a solution of Ø-(PIB-$CH_2$—$CH_2$—$CH_2$—Br)$_3$ in THF. Then an aqueous solution of NaOH is added, and the charge is stirred for 2 hours at room temperature. Optionally, a phase transfer catalyst such as tetraethyl ammonium bromide can be added to speed up the reaction. The product is then washed 3 times with water, dried over magnesium sulfate overnight and filtered. Finally the solvent is removed via the use of a rotary evaporator. The product, a primary alcohol-terminated PIB product, is a clear viscous liquid.

Example 9

Synthesis of the Polyurethane

The allyl di-telechelic PIB of Example 5 containing the residue of the bBCB-ol initiator is first dissolved in heptane. Air is then bubbled through the solution for 30 minutes at 100° C. to activate the allylic end groups. The solution is then cooled to approximately −10° C. and HBr gas is bubbled through the system for 10 minutes to produce the corresponding Br-di-telechelic PIB. After neutralizing the solution with aqueous $NaHCO_3$ (10%), the product is washed 3 times with water. Finally the solution is dried over magnesium sulfate for at least 12 hours (i.e., overnight) and filtered. The solvent is then removed via a rotary evaporator. The Br-PIB-Br product is a clear viscous liquid.

The conversion of the terminal bromine group to a terminal primary hydroxyl group is performed by nucleophilic substitution on the bromine as follows. The Br-PIB-Br product is first dissolved in THF. Then, an aqueous solution of NaOH is added, and the charge is stirred for 2 hours at room temperature. Optionally, a phase transfer catalyst such as tetraethyl ammonium bromide can be added to speed up the reaction. The product is then washed 3 times with water, dried over magnesium sulfate overnight and filtered. Finally the solvent is removed via the use of a rotary evaporator. The product, a primary alcohol-terminated PIB product contains the residue of the bBCB-ol initiator.

The HO-PIB-OH above is next dissolved in dry toluene and freshly distilled MDI and tin dioctoate catalyst are added under a dry nitrogen atmosphere. The charge is then heated for 8 hours at 70° C., cooled to room temperature, and poured in a rectangular (5 cm×5 cm) Teflon mold. The system is air dried overnight and finally dried in a drying oven at 70° C. for 24 hours to produce a PIB polyurethane containing the residue of the bBCB-ol initiator.

Example 10

Synthesis of the Amine Telechelic PIB 30 grams of allyl di-telechelic PIB polymer (Allyl-PIB-Allyl) is combined with 150 mL of heptane and refluxed at 110° C. for about 30 minutes, followed by passing HBr gas over the polymer solutions for 5 minutes at 0° C. to convert the Allyl-PIB-Allyl polymer to the corresponding telechelic primary bromide polymer (Br—$(CH_2)_3$-PIB-$(CH_2)_3$—Br)

Next, the Br—$(CH_2)_3$-PIB-$(CH_2)_3$—Br is converted by using: (1) potassium phthalimide; and (2) hydrazine hydrate to yield the target ditelechelic amine, $NH_2$—$(CH_2)_3$-PIB-$(CH_2)_3$—$NH_2$ by the following process. 16 grams of bromo-ditelechelic polyisobutylene (0.003 mol) is dissolved in 320 mL dry THF. Then, 160 mL of N-methyl-2-pyrrolidone (NMP) and phthalimide potassium (2.2 grams, 0.012 moles) are added to this solution. Next, the solution is heated to reflux at 80° C. for 8 hours. The product is then dissolved in 100 mL of hexane, extracted 3 times with water, and dried over magnesium sulfate. Then, the phthalimide-telechelic polyisobutylene (14 grams, 0.0025 moles) is dissolved in 280 mL of heptane, then 280 mL of ethanol and hydrazine hydrate (3.2 grams, 0.1 moles) are added thereto, and the solution is heated to reflux at 110° C. for 6 hours. The product is dissolved in hexane, extracted 3 times with water, dried over magnesium sulfate, and the hexane is removed by a rotary evaporator (rotavap) to provide the allyl di-telechelic PIB polymer.

Example 11

Synthesis of the Polyurea

To $H_2N$-PIB-$NH_2$ (1.5 grams, $M_n$=5,500 g/mol, amine equivalent 0.00054 moles) dissolved in dry toluene (10 mL) is added freshly distilled MDI (0.125 grams, 0.0005 moles), with stirring, under a dry nitrogen atmosphere. Within a minute the solution becomes viscous. It is then diluted with 5 mL of toluene and poured in a rectangular (5 cm×5 cm) Teflon mold. The system is air dried overnight and finally dried in a drying oven at 70° C. for 24 hours. The polyurea product is a pale yellow supple rubbery sheet, soluble in THF.

Example 12

Synthesis of Polyisobutylene-Polystyrene Block Copolymer

Into a 300 mL round bottom flask equipped with a magnetic stirrer is placed 30 mL dried and distilled hexane, 20 mL dried and distilled dichloromethane and DtBP (5.0× $10^{-5}$ mol) proton trap and cooled to −80° C. Under strong stirring 7.7×$10^{-2}$ g (3.0×$10^{-4}$ mol) bBdClCB is added and the system stirred for 5 min. Then 4.6 mL (5.3×$10^{-2}$ mol) IB is added followed by the addition of 0.7 mL (6.0×$10^{-3}$ mol) TiCl$_4$. The polymerization is allowed to proceed for about 60 min and then 1.8 mL (1.6×$10^{-2}$ mol) styrene is added. After 1 hour polymerization is terminated with ~5 mL methanol. The reactor is removed from the cooling bath and allowed to warm to room temperature. The solution is concentrated by rotary evaporation, precipitated into ~100 mL methanol, the methanol is decanted, the polymer dissolved in hexane, and is washed with 5% aqueous sodium bicarbonate and water. The organic phase is dried over night over magnesium sulfate, and filtered through fine sintered glass. Finally, the solvent is evaporated by rotary evaporation and the product is dried in high vacuum.

In light of the foregoing, it should be appreciated that the present invention significantly advances the art by providing a novel, low cost LC$^+$P initiator that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A telechelic polyisobutylene composition comprising a residue of a bifunctional initiator molecule having the formula:

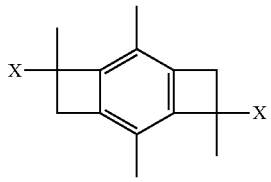

wherein x is Cl, OH, or OCH$_3$, and wherein the residue of the bifunctional initiator molecule prevents intramolecular aromatic alkylation.

2. The telechelic polyisobutylene composition as claimed in claim 1, comprising two polyisobutylene chains extending from said Initiator molecule residue, and wherein each of said two polyisobutylene chains further comprises a terminal functional group.

3. The telechelic polyisobutylene composition as claimed in claim 2, wherein each of said terminal functional groups is selected from the group consisting of allyl groups, hydroxyl groups, primary or tertiary alcohols, halides, amine groups, azide groups, thiol groups furanyl groups, alkynyl groups, cyano groups, and combinations thereof.

4. The telechelic polyisobutylene composition as claimed in claim 3, wherein said terminal functional groups are allyl groups, the composition having the formula:

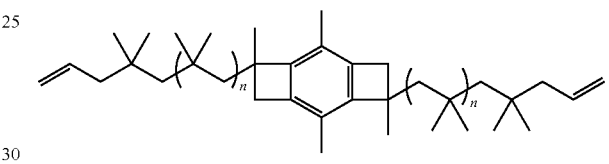

wherein each individual n is an integer from 2 to about 5,000.

5. The telechelic polyisobutylene composition as claimed in claim 3, wherein said terminal functional groups are hydroxy groups, the composition having the formula:

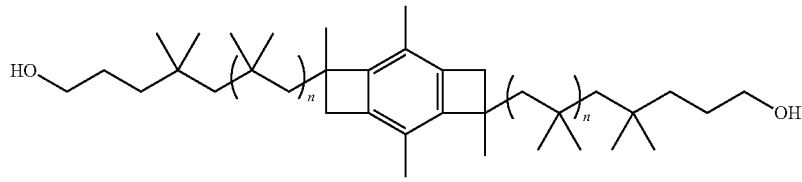

wherein each individual n is an integer from 2 to 5,000.

6. The telechelic polyisobutylene composition as claimed in claim 3, wherein said terminal functional groups are amine groups, the composition having the formula:

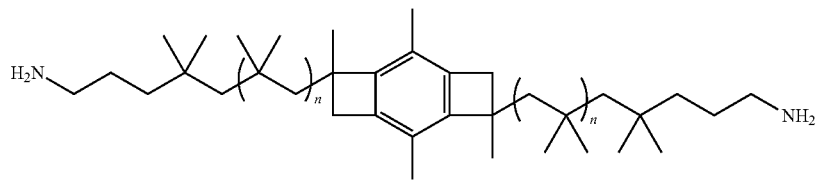

wherein each individual n is an integer from 2 to 5,000.

7. The telechelic polyisobutylene composition as claimed in claim 3, wherein one of said terminal functional groups is a hydroxyl group and another of said terminal functional groups is an amine group.

8. A polyisobutylene-based polyurethane comprising the reaction product of a diisocyanate and the —OH terminated polyisobutylene as claimed in claim 5.

9. The polyisobutylene-based polyurethane as claimed in claim 8 having the formula:

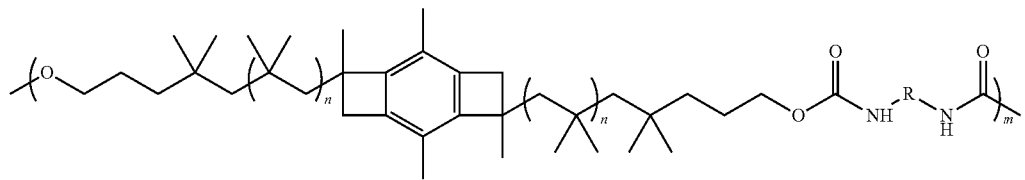

where each n is an integer from 2 to 5,000, m is an integer from 2 to 1,000,000, and R is a residue of toluene diisocyanate or 4, 4'-diphenylmethane diisocyanate having the formula:

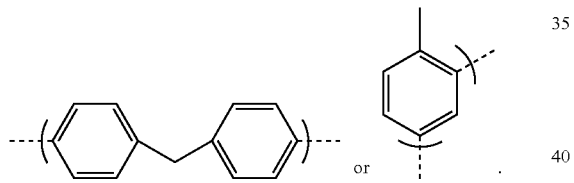

10. A polyisobutylene-based polyurea comprising the reaction product of a diisocyanate and the amine-terminated polyisobutylene composition as claimed in claim 6.

11. A polyisobutylene-based polyurethane/polyurea comprising the reaction product of a diisocyanate and the composition having the hydro-terminated polyisobutylene at one end and amine-terminated polyisobutylene at the other end as claimed in claim 7.

12. The polyisobutylene-based polyurethane/polyurea as claimed in claim 11 having having the formula:

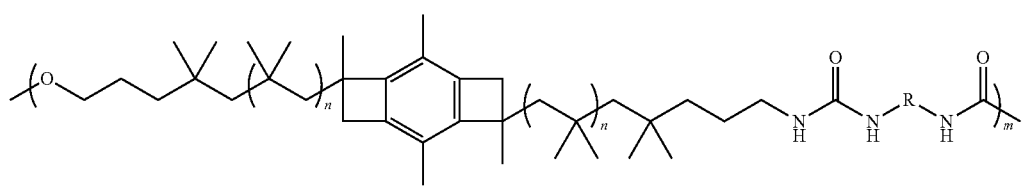

where each n is an integer from 2 to 5,000, m is an integer from 2 to 1,000,000, and R is a residue of toluene diisocyanate or 4, 4'-diphenylmethane diisocyanate having the formula:

13. A method for making the bifunctional initiator molecule as claimed in claim 1 comprising:

A. dissolving 1,2,4,5-tetramethyl benzene or 1,2,3,5-tetramethyl benzene in a suitable solvent;

B. combining an acetyl halide, aluminum chloride, and a dry solvent in a suitable container and heating it to reflux for from about 6 to about 12 hours;

C. adding the solution of step A to the solution of step B and stirring at reflux for an additional 10 to 14 hours;

D. separating the resulting polymer containing solution into organic and aqueous phases, washing the resulting organic phase with aqueous sodium carbonate, removing the solvent, and drying the resulting product to produce the corresponding diethanone;

E. dissolving said corresponding diethanone in a suitable solvent and irradiating it with ultraviolet light to form the corresponding bis-benzocyclobutenol initiator molecule.

14. The method as claimed in claim 13 further comprising:
   F. hydrochlorinating the bis-benzocyclobutenol initiator molecule of Step E to form the corresponding dichloro initiator molecule.

* * * * *